(12) United States Patent
Schoenfisch et al.

US012257314B2

(10) Patent No.: US 12,257,314 B2
(45) Date of Patent: Mar. 25, 2025

(54) EXTENDED NITRIC OXIDE-RELEASING POLYMERS VIA FUNCTIONALIZED MESOPOROUS SILICA NANOPARTICLES

(71) Applicant: The University of North Carolina at Chapel Hill, Chapel Hill, NC (US)

(72) Inventors: Mark H. Schoenfisch, Chapel Hill, NC (US); Maggie Malone-Povolny, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 706 days.

(21) Appl. No.: 17/435,313

(22) PCT Filed: Feb. 28, 2020

(86) PCT No.: PCT/US2020/020443
§ 371 (c)(1),
(2) Date: Aug. 31, 2021

(87) PCT Pub. No.: WO2020/180705
PCT Pub. Date: Sep. 10, 2020

(65) Prior Publication Data
US 2022/0152219 A1 May 19, 2022

Related U.S. Application Data

(60) Provisional application No. 62/812,735, filed on Mar. 1, 2019.

(51) Int. Cl.
*A61K 47/69* (2017.01)
*A61K 9/14* (2006.01)
*A61K 33/00* (2006.01)

(52) U.S. Cl.
CPC .......... *A61K 47/6923* (2017.08); *A61K 9/146* (2013.01); *A61K 33/00* (2013.01); *A61K 47/6929* (2017.08)

(58) Field of Classification Search
CPC ............ A61K 47/6923; A61K 47/6929; A61K 9/146; A61K 33/00
See application file for complete search history.

(56) References Cited

U.S. PATENT DOCUMENTS

| 5,234,933 | A | 8/1993 | Marnett et al. |
| 5,326,902 | A | 7/1994 | Seipp et al. |
| 6,180,082 | B1 | 1/2001 | Woltering et al. |
| 2009/0214618 | A1 | 8/2009 | Schoenfisch et al. |
| 2011/0151000 | A1 | 6/2011 | Schultz et al. |
| 2019/0039910 | A1 | 2/2019 | Handa et al. |

FOREIGN PATENT DOCUMENTS

| WO | WO 93/25521 | 12/1993 |
| WO | WO 2012/118819 A2 | 9/2012 |
| WO | WO 2017/079268 | 5/2017 |

OTHER PUBLICATIONS

Akindoyo, J.O. et al., "Polyurethane Types, Synthesis and Applications—a Review," RSC Adv., 6:114453-114482, (2016).
Bogdan, C., "Nitric Oxide and the Immune Response," Nat. Immunol., 2:907-916, (2001).
Carpenter, A.W. et al., "Nitric Oxide Release: Part II. Therapeutic Applications," Chem. Soc. Rev., 41:3742-3752, (2012).
Chen, Y. et al., "In Vivo Bio-Safety Evaluations and Diagnostic/Therapeutic Applications of Chemically Designed Mesoporous Silica Nanoparticles," Adv. Mater., 25:3144-3176, (2013).
Chou, H. et al., "Direct Formation of S-Nitroso Silica Nanoparticles from a Single Silica Source," Langmuir, 30:812-822, (2014).
Cleeter, M.W. et al., "Reversible Inhibition of Cytochrome c Oxidase, the Terminal Enzyme of the Mitochondrial Respiratory Chain, by Nitric Oxide. Implications for Neurodegenerative Diseases," Fed. Eur. Biochem. Soc. Lett., 345:50-54, (1994).
Coneski, P.N. et al., "Nitric Oxide Release: Part III. Measurement and Reporting," Chem. Soc. Rev., 41:3753-3758, (2012).
Cooke, J.P., "No. and Angiogenesis," Atherosclerosis 4:53-60, (2003).
Davis, F.J. et al., "Polyurethane Based Materials with Applications in Medical Devices," Bio-Materials and Prototyping Applications in Medicine, 27-48, (2008).
De Groote M.A. et al., "NO Inhibitions: Antimicrobial Properties of Nitric Oxide," Oxford Univ. Press, 21:162-165, (1995).
De Oliveira, M. et al., "Thermal Stability of Primary S-Nitrosothiols: Roles of Autocatalysis and Structural Effects on the Rate of Nitric Oxide Release," J. Phys. Chem. A, 106:8963-8970, (2002).
Denisov, E.T., "Cage Effects in a Polymer Matrix," Macromol. Chem. Phys., 8:63-78, (1984).
Dolatzadeh, F. et al., "Influence of Various Loadings of Hydrophilic or Hydrophobic Silica Nanoparticles on Water Uptake and Porosity of a Polyurethane Coating," Mater. Corros., 64:609-618, (2013).
Duch, D.S. et al., "Volatile anesthetics significantly suppress central and peripheral mammalian sodium channels," Toxicol. Lett., 100-101:255-263, (1998).
Ellman, G.L., "Tissue Sulfhydryl Groups," Arch. Biochem. Biophys., 82:70-77, (1959).
Fischer, U., "Fundamentals of Glucose Sensors," Diabet. Med., 8:309-321, (1991).
Franck, J. et al., "Free Radicals and the Photochemistry of Solutions," Trans. Faraday Soc.., 30:120-130, (1934).
Freireich et al., Cancer Chemother Rep., 50:219-244, (1966).
Frost, M.C. et al., "Synthesis, characterization, and controlled nitric oxide release from S-nitrosothiol-derivatized fumed silica polymer filler particles," J. Biomed. Mater. Res., 72A:409-419, (2005).
Frungillo, L. et al., "Modulation of Mitochondrial Activity by S-Nitrosoglutathione Reductase in *Arabidopsis thaliana* Transgenic Cell Lines," Biochim. Biophys. Acta, 1827:239-247, (2013).
Grommersch, Bryan et al., "Biotemplated Synthesis and Characterization of Mesoporous Nitric Oxide-Releasing Diatomaceous Earth Silica Particles," ACS Appl. Mater. Interfaces, 10:2291-2301, (2018).
Haj-Ahmad, R. et al., "Microneedle Coating Techniques for Transdermal Drug Delivery," Pharmaceutics, 7:486-502, (2015).

(Continued)

*Primary Examiner* — Shirley V Gembeh
(74) *Attorney, Agent, or Firm* — Alston & Bird LLP

(57) ABSTRACT

The subject matter disclosed herein is directed to nitric oxide releasing particles comprising a mesoporous silica network. Also disclosed are compositions comprising one or more nitric-oxide releasing particles and a polymer. In one aspect, the particles are admixed with the polymer. The compositions exhibit high payloads of nitric oxide release without particle leaching or the need for extremely cold storage conditions.

18 Claims, 5 Drawing Sheets

(56) References Cited

OTHER PUBLICATIONS

Hakim et al., "Half-Life of Nitric Oxide in Aqueous Solutions with and without Haemoglobin," Physiol. Meas., 17:267-277, (1996).
Ibrahim, I.A. et al., "Preparation of Spherical Silica Nanoparticles: Stober Silica," J. Am. Sci., 6:985-989, (2010).
Koh, A. et al., "Fabrication of Nitric Oxide-Releasing Polyurethane Glucose Sensor Membranes," Biosens. Bioelectron., 28:17-24, (2011).
Koh, A. et al., "Glucose Sensor Membranes for Mitigating the Foreign Body Response," J. Diabetes Sci. Technol., 5:1052-1059, (2011).
Koh, A. et al., "Nitric Oxide-Releasing Silica Nanoparticle-Doped Polyurethane Electrospun Fibers," ACS Appl. Mater. Interfaces, 5:7956-7964, (2013).
Kruk, M. et al., "Gas Adsorption Characterization of Ordered Organic-Inorganic Nanocomposite Materials," Chem. Mater., 13:3169-3183, (2001).
Lin, Y.-S. et al., "Impacts of Mesoporous Silica Nanoparticle Size, Pore Ordering, and Pore Integrity on Hemolytic Activity," J. Am. Chem. Soc., 132:4834-4842, (2010).
Liu, T. et al., "Hollow Polymer Nanoparticles with S-Nitrosothiols as Scaffolds for Nitric Oxide Release," J. Colloid Interface Sci., 459:115-122, (2015).
Lu, Y. et al., "Nitric Oxide-Releasing Chitosan Oligosaccharides as Antibacterial Agents," Biomaterials, 35:1716-1724, (2014).
Malone-Povolny, et al., "Extended Nitric Oxide-Releasing Polyurethanes via S-Nitrosothiol-Modified Mesoporous Silica Nanoparticles," ACS Applied Materials & Interfaces, 11(13):12216-12223, (2019).
Minko, S., "Grafting on Solid Surfaces: "Grafting to" and "Grafting from" Methods," Polymer Surfaces and Interfaces, 215-234, (2008).
Murugadoss, S. et al., "Toxicology of Silica Nanoparticles: An Update," Arch. Toxicol., 91:2967-3010, (2017).
Norton, L. et al., "Vascular Endothelial Growth Factor and Dexamethasone Release from Nonfouling Sensor Coatings Affect the Foreign Body Response," J. Biomed. Mater. Res., 81A:858-869, (2007).
Pegalajar-Jurado, A. et al., "Nitric Oxide-Releasing Polysaccharide Derivative Exhibits 8-Log Reduction against *Escherichia coli*, Acinetobacter Baumannii and *Staphylococcus aureus*," J. Control. Release, 220B:617-623, (2015).
Rabinowitch, E. et al., "The collison mechanism and the primary photochemical process in solutions," Trans. Faraday Soc.., 32:1381-1387, (1936).
Rashti, A. et al., "Development of Novel Biocompatible Hybrid Nanocomposites Based on Polyurethane-Silica Prepared by Sol Gel Process," Mater. Sci. Eng. C, 69:1248-1255, (2016).
Ren, H. et al., "Thromboresistant/Anti-Biofilm Catheters via Electrochemically Modulated Nitric Oxide Release," Bioelectrochemistry, 104:10-16, (2015).
Riccio, D. et al., "Stober Synthesis of Nitric Oxide-Releasing S-Nitrosothiol-Modified Silica Particles," Chem. Mater., 23:1727-1735, (2011).
Seabra, A.B. et al., "Nitric oxide-releasing vehicles for biomedical applications," J. Mater. Chem., 20:1624-1637, (2010).
Seo, E. et al., "Polyurethane Membrane with Porous Surface for Controlled Drug Release in Drug Eluting Stent," Biomater. Res., 18:15, (2014).
Shishido, S. et al., "Polyethylene Glycol Matrix Reduces the Rates of Photochemical and Thermal Release of Nitric Oxide from S-Nitroso-N-Acetylcysteine," Photochem. Photobiol., 71:273-280, (2007).
Shishido, S. et al., "Thermal and Photochemical Nitric Oxide Release from S-Nitrosothiols Incorporated in Pluronic F127 Gel: Potential Uses for Local and Controlled Nitric Oxide Release," Biomaterials, 24:3543-3553, (2003).
Slomberg, D. et al., "Role of Size and Shape on Biofilm Eradication for Nitric Oxide-Releasing Silica Nanoparticles," ACS Appl. Mater. Interfaces, 5:9322-9329, (2013).
Soto, R. et al., "In Vivo Analytical Performance of Nitric Oxide-Releasing Glucose Biosensors," Anal. Chem., 86:7141-7149, (2014).
Soto, R.J. et al., "Design Considerations for Silica Particle-Doped Nitric OxideReleasing Polyurethane Glucose Biosensor Membranes," ACS Sensors , 2:140-150, (2017).
Soto, R.J. et al., "Functionalized Mesoporous Silica via an Aminosilane Surfactant Ion Exchange Reaction: Controlled Scaffold Design and Nitric Oxide Release," ACS Appl. Mater. Interfaces, 8:2220-2231, (2016).
Stamler, J.S et al., "The Decomposition of Thionitrites," Curr. Opin. Chem. Biol., 6:779-785, (2002).
Stasko, N.A. et al., "S-Nitrosothiol-Modified Dendrimers as Nitric Oxide Delivery Vehicles," Biomacromolecules, 9:834-841 (2008).
Sun, B. et al., "Nitric Oxide-Releasing Dendrimers as Antibacterial Agents, "Biomacromolecules, 13:3343-3354, (2012).
Thomas, D.D. et al., "The Chemical Biology of Nitric Oxide: Implications in Cellular Signaling," Free Radic. Biol. Med., 45:18-31, (2008).
Treter, J. et al., "Catheters: A Suitable Surface for Biofilm Formation," Science Against Microbial Pathogens: Communicating Current Research and Technological Advances, 835-842, (2011).
Varu, Vinit N. et al., "Nitric Oxide-Releasing Prosthetic Materials," Vasc. Endovascular Surg., 43:121-131, (2009).
Wang, Y. et al., "Foreign Body Reaction to Implantable Biosensors: Effects of Tissue Trauma and Implant Size," J. Diabetes Sci. Technol., 9:966-977, (2015).
Ward, W.K. et al., "A New Amperometric Glucose Microsensor: In Vitro and Short-Term in Vivo Evaluation," Biosens. Bioelectron., 17:181-189 (2002).
Williams, D.L.H., "The Chemistry of S-Nitrosothiols," Acc. Chem. Res., 32:869-876, (2002).
Witte, M.B. et al., "Role of Nitric Oxide in Wound Repair," Am. J. Surg., 183:406-412, (2002).
Wolf, A. et al., "Improved Thromboresistance and Analytical Performance of Intravascular Amperometric Glucose Sensors Using Optimized Nitric Oxide Release Coatings," Chinese Chem. Lett., 26:464-468, (2015).
Wrzeszcz, A. et al., "Dexamethasone Released from Cochlear Implant Coatings Combined with a Protein Repellent Hydrogel Layer Inhibits Fibroblast Proliferation," J. Biomed. Mater. Res. A, 102:442-454, (2014).
Yang, L. et al., "S-Nitrosothiol-Modified Hyperbranched Polyesters," Polym. Chem., 7:7161-7169, (2016).
Yu, T. et al., "Influence of Geometry, Porosity, and Surface Characteristics of Silica Nanoparticles on Acute Toxicity: Their Vasculature Effect and Tolerance Threshold," ACS Nano, 6:2289-2301, (2012).
Zanini, S. et al., "Development of Antibacterial Quaternary Ammonium Silane Coatings on Polyurethane Catheters," J. Colloid Interface Sci., 451:78-84, (2015).
WIPO Application No. PCT/US2020/020443, PCT International Search Report and Written Opinion of the International Searching Authority mailed Jun. 29, 2020.

EXTENDED NITRIC OXIDE-RELEASING POLYMERS VIA FUNCTIONALIZED MESOPOROUS SILICA NANOPARTICLES

CROSS-REFERENCE TO RELATED APPLICATIONS

This application is a 35 U.S.C. § 371 national stage of International Application No. PCT/US2020/020443, filed Feb. 28, 2020, which claims the benefit of priority to U.S. Provisional Application No. 62/812,735 filed Mar. 1, 2019, which are herein incorporated by reference in their entirety for all purposes.

GOVERNMENT INTEREST

This invention was made with government support under Grant No. DK108318 awarded by The National Institutes of Health. The Government has certain rights in the invention.

FIELD OF THE INVENTION

The presently disclosed subject matter relates generally to extended nitric oxide-releasing particles. In some embodiments, the presently disclosed subject matter provides a composition comprising one or more nitric oxide releasing particles and a polymer that releases nitric oxide with large payloads and in an extended manner.

BACKGROUND

Nitric oxide (NO), an endogenously produced free radical, plays a role in numerous physiological processes, including the inflammatory response, angiogenesis, vasodilation, and antimicrobial and tumoricidal activity.[1-5] In vivo, nitric oxide synthase (NOS) enzymes generate NO at concentrations (nM-µM) and kinetics dependent on the enzyme location and purpose. For example, low concentrations of NO generated via calcium-dependent endothelial and neuronal NOS regulate neovascularization and serve roles in neurotransmission. Activation of the inducible NOS isoform by immunological stimuli (e.g., lipopolysaccharide, interferon-γ) causes sustained NO release at high concentrations to eradicate foreign pathogens as part of the innate immune response. The multifaceted roles of endogenous NO are attributable to precise spatiotemporal NO release by cells expressing the NOS enzymes. In addition, NO's short biological lifetime (seconds) restricts its action to <0.5 mm from the point of generation.

Due to NO's overwhelming presence in physiology, the administration of exogenous NO gas represents a potential therapy for many diseases. A significant body of research has focused on the development of donors that store and release NO under specific chemical conditions in order to address the concentration-dependent behavior of NO and avoid challenges associated with the administration of NO directly, such as the need for a pressurized gas cylinder and NO's rapid reaction in biological media. In particular, nitric oxide's role in wound healing has motivated the development of medical devices with NO-release capabilities to improve tissue integration and device performance. The development of a range of NO-releasing molecular scaffolds, including nanoparticles, polysaccharides, and dendrimers, has provided NO-release systems with a wide array of scaffold characteristics and release profiles to suit multiple medical applications. However, there still remains a need in the art for more efficient and effective NO-delivery systems to achieve targeted, tunable, and extended delivery of NO. This problem is addressed by the subject matter described herein.

BRIEF SUMMARY

In one aspect, the presently disclosed subject matter provides a nitric oxide releasing particle, comprising:
  nitric oxide donors;
  a mesoporous silica network; and
  an exterior surface,
    wherein said nitric oxide donors are present within pores of said mesoporous silica network and on the exterior surface of said particle, and
    wherein said nitric oxide releasing particle comprises an amount of nitric oxide donors such that the particle exhibits a total nitric oxide release duration of at least 49 hours.

In another aspect, the presently disclosed subject matter provides a composition comprising one or more nitric oxide releasing particles and a polymer.

DETAILED DESCRIPTION

Figure 1A:
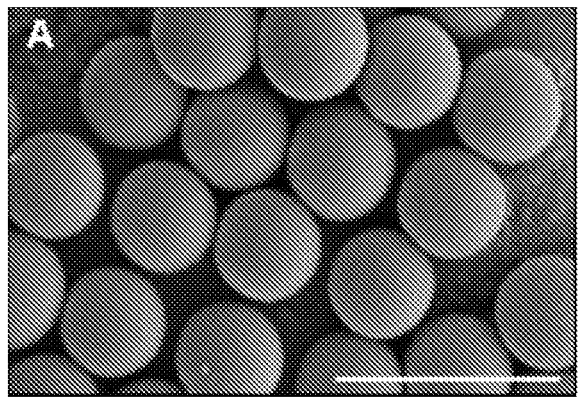
FIG. 1A shows a scanning electron micrograph of bare TEOS MSNs. The scale bar represents 2 µm.

Disclosed herein are mesoporous silica particles functionalized with a nitric oxide donor that exhibit large nitric oxide release payloads and extended nitric oxide release durations. In certain embodiments, the nitric oxide donor comprises an s-nitrosothiol functional group. Also disclosed are compositions comprising one or more nitric oxide releasing particles admixed with a polymer, which achieve nitric oxide release durations of at least 20 days without particle leaching or the need for extremely cold storage conditions. In some embodiments, the polymer is a polyurethane. The nitric oxide release kinetics of the nitric oxide releasing particle and polymer compositions are consistent over a range of polyurethane properties and are essentially independent of water uptake. These attributes present new opportunities for introducing the benefits of nitric oxide to a wider range of medical devices, where polyurethane composition selection is often tied to a given device's need or utility.

Many different strategies for the active release of drugs from a medical device have been investigated. Several of these include outer coatings doped with traditional antibiotics to limit infection,[10] dexamethasone to reduce inflammation,[11] or gene therapeutic agents to stimulate vascular growth.[12] Nitric oxide is unique in that it is capable of providing each of these benefits in a single drug-release configuration. In particular, silica nanoparticles (SNPs) represent an attractive NO-releasing macromolecular scaffold for medical device coatings. Silica is bioinert, easily functionalizable, and can be readily encapsulated in the polymeric coatings commonly used in the design and fabrication of a given device.[18-20] Preliminary studies using SNP-based NO-releasing intravascular catheter coatings and subcutaneous glucose sensor membranes have shown reduced thrombosis and tissue inflammation, respectively.[21,22] The promising results from these studies prompted the development of more efficient and effective NO-delivery systems to achieve targeted, tunable, and extended delivery of NO from polymeric coatings. Extended release durations, in particular, have been implicated in better device outcomes: lower thrombosis, improved analyte uptake into microneedles, and decreased inflammatory tissue markers.[22-24]

Previous investigations related to NO-releasing SNP-doped coatings have primarily focused on N-diazeniumdiolate (NONOate)-modified SNPs.[13,22,25] The decomposition rate of NONOates (and liberation of NO) relies on the uptake of water (protons) by the polymer, which imposes a restriction on the design of the system, wherein hydrophobic matrices are required to extend the release of NO. Such requirement is challenging for applications that favor more hydrophilic materials to prevent biofouling (e.g., wound dressings and implanted sensors). In contrast, the use of S-nitrosothiol (RSNO) NO donors does not impose the same design restrictions as NONOates, as the NO release from RSNOs is based on a photothermal decomposition mechanism, independent of water uptake or local pH. While the lability of RSNOs species allows them to release NO spontaneously under physiological conditions, photothermal instability is detrimental with respect to storage of the material. Previous work has emphasized that RSNO-based scaffolds are susceptible to ambient light and heat, which poses a challenge for their translation to large-scale commercial distribution.[26-28]

Mesoporous silica nanoparticles (MSNs) are SNPs with an array of mesochannels that may address the stability challenges commonly associated with RSNO-modified SNPs. The inherently large interior surface area of MSNs may confer additional stability to intraporous RSNO groups due to a phenomenon known as the cage effect. First defined by Franck and Rabinowitch,[29,30] the cage effect describes the reduction of radical species formation via geminate recombination within the confines of strong solvent "cages." These cages are formed by viscous solvents and/or local structural confinement.[31,32] In the case of RSNOs, the cage effect favors recombination of the thiyl and NO radical pair after homolytic S—N bond cleavage, extending the duration of NO delivery.[33,34] The confined microenvironment provided by the nanometer-scale pores of an MSN may reduce the rate of thermal and photochemical NO release in comparison to RSNO groups found on the exterior surface area of a particle.

The synthesis of S-nitrosothiol-functionalized silica nanoparticles with nonporous, hollow, diatomaceous, and fumed morphologies has been described in the art.[26,27,39,40] In particular, WO 2017/079268 discloses the preparation of functionalized mesoporous silica nanoparticles through a surfactant ion exchange reaction, the contents of which are incorporated herein by reference. Confined microenvironments provided by organic polymers have been shown to lead to greater RSNO radical pair recombination compared to those with less rigid milieus.[41] The synthetic protocol of the present disclosure was therefore developed on the basis that a novel and effective path for enhancing the stability of RSNO-functionalized nanoparticles would result from porosity within a silica particle network. Furthermore, the increased specific surface area of the MSNs would allow for larger NO payloads as compared to nonporous analogues.

To take advantage of the impact of mesoporosity on NO stabilization, the synthetic process described herein was implemented to functionalize silica nanoparticles with RSNO donors both on the exterior surface and within the pores. In this manner, the mercaptosilanes were post-grafted onto the MSNs to achieve greater functional group grafting density.[42] The mesoporous silica nanoparticles made of the backbone silane TEOS were synthesized through a modified Stöber method in the presence of a liquid crystal surfactant template.[35] After particle formation, the surfactant was removed by ion exchange with acid, allowing the surface silanols to be activated by oxygen plasma treatment. Finally, the MSNs were post-grafted with a primary mercaptosilane, MPTMS, by refluxing in base-catalyzed DMF. Optimization of the synthetic procedure identified ideal reflux solvent, reflux temperature, and mercaptosilane concentration in order to achieve monodisperse, densely-grafted RSNO-modified MSNs.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. Unless otherwise defined, all technical and scientific terms used herein have the same meaning as commonly understood by one of ordinary skill in this field. All publications, patent applications, patents, and other references mentioned herein are incorporated by reference in their entirety. In the event that one or more of the incorporated literature, patents, and similar materials differs from or contradicts this application, including but not limited to defined terms, term usage, described techniques, or the like, this application controls.

As used herein, "and/or" refers to and encompasses any and all possible combinations of one or more of the associated listed items, as well as the lack of combinations when interpreted in the alternative ("or").

As used herein, the term "about," when referring to a measurable value such as an amount of a compound or agent of the current subject matter, dose, time, temperature, and the like, is meant to encompass variations of ±20%, ±10%, ±5%, ±1%, ±0.5%, or even ±0.1% of the specified amount.

The terms "approximately," "about," "essentially," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic.

As used herein, conditional language used herein, such as, among others, "can," "could," "might," "may," "e.g.," and the like, unless specifically stated otherwise or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "nitric oxide donor" or "NO donor" refer to species and/or molecules that donate, release and/or directly or indirectly transfer a nitric oxide species (i.e. (NO+, NO−, NO (e.g., •NO))), and/or stimulate the endogenous production of nitric oxide in vivo and/or elevate endogenous levels of nitric oxide in vivo such that the biological activity of the nitric oxide species is expressed at the intended site of action.

The terms "nitric oxide releasing" or "nitric oxide donating" refer to species that donate, release and/or directly or indirectly transfer any one (or two or more) of the three redox forms of nitrogen monoxide (NO+, NO−, NO (e.g., •NO)) and/or methods of donating, releasing and/or directly or indirectly transferring any one (or two or more) of the three redox forms of nitrogen monoxide (NO+, NO−, NO). In some embodiments, the nitric oxide releasing is accomplished such that the biological activity of the nitrogen monoxide species is expressed at the intended site of action.

The term "hydrophobic" refers to a chemical compound or moiety that, to a given extent, repels or does not interact with water through non-covalent forces such as hydrogen bonding or electrostatic interactions. A compound can be strongly hydrophobic or slightly hydrophobic. The calculated dielectric constant of a compound or group can be used to predict the level or degree of hydrophobicity of the compound or moiety. Compounds or moieties with lower dielectric constants will be more hydrophobic. In particular, a "hydrophobic linker" is one that will protect a labile linker or a NO donor in a NO-releasing particle from exposure to water when the particle is placed in an aqueous environment for a period of time. A more hydrophobic linker will protect a NO donor or labile linker from water for a longer period of time.

The term "hydrophilic" refers to a compound or moiety that will interact with water to given extent.

The term "ionizable" refers to a group that is electronically neutral (La, uncharged) in a particular chemical environment (e.g., at a particular pH), but that can be ionized and thus rendered positively or negatively charged in another chemical environment (e.g., at a higher or lower pH).

The term "mesoporous" as used herein refers to an object, such as a particle, comprising pores in the range of between about 20-500 angstroms.

The term "MSN" refers to mesoporous silica nanoparticles.

The term, "CTAB" refers to cetyltrimethyl ammonium bromide.

The term, "TEOS" refers to tetraethyl orthosilicate.

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), 1 to 4 carbon atoms (i.e., $C_{1-4}$ alkyl), or 1 to 3 carbon atoms (i.e., $C_{1-3}$ alkyl). Examples of alkyl groups include, e.g., methyl, ethyl, propyl, isopropyl, n-butyl, secbutyl, iso-butyl, tert-butyl, pentyl, 2-pentyl, iso-pentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., $—(CH_2)_3CH_3$), sec-butyl (i.e., $—CH(CH_3)CH_2CH_3$), isobutyl (i.e., $—CH_2CH(CH_3)_2$) and tert-butyl (i.e., $—C(CH_3)_3$); and "propyl" includes n-propyl (i.e., $—(CH_2)_2CH_3$) and isopropyl (i.e., $—CH(CH_3)_2$). "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl, "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl) or 2 to 4 carbon atoms (i.e., $C_{2-4}$ alkenyl). Examples of alkenyl groups include, e.g., ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl) or 2 to 4 carbon atoms (i.e., $C_{2-4}$ alkynyl). The term "alkynyl" also includes those groups having one triple bond and one double bond.

Alkyl, alkenyl, and alkynyl groups can optionally be substituted with one or more substituents, which can be the same or different. The terms "alkyl group substituent," "alkenyl group substituent," and "alkynyl group substituent" include but are not limited to alkyl, alkynyl, alkenyl, substituted alkenyl, substituted alkyl, halo, arylamino, acyl, hydroxyl, aryloxyl, alkoxyl, alkylthio, arylthio, aralkyloxyl, araikylthio, carboxyl, alkoxycarbonyl, oxo, and cycloalkyl. There can be optionally inserted along the alkyl, alkenyl, or alkynyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the terms "substituted alkyl" "substituted alkenyl," and "substituted alkynyl" include alkyl, alkenyl, and alkynyl groups, as defined herein, in which one or more atoms or functional groups of the alkyl, alkenyl, and alkynyl groups are replaced with another atom or functional group, including for example, alkyl, alkenyl, alkynyl, substituted alkyl, substituted alkenyl, substituted alkynyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, Including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, two, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein can refer to, for example, methoxyl, ethoxyl, propoxyl, isopropoxyl, butoxyl, t-butoxyl, and pentoxyl. The term "oxyalky" can be used interchangeably with "alkoxyl".

"Aralkyl" refers to an aryl-alkyl- group wherein aryl and alkyl are as previously described, and included substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 5, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons.

"Arylene" refers to a bivalent aryl group. An exemplary arylene is phenylene, which can have ring carbon atoms available for bonding in ortho, meta, or para positions with regard to each other, i.e.,

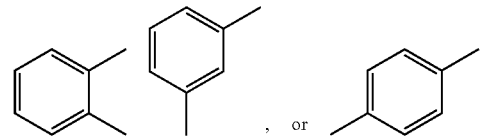

respectively. The arylene group can also be naphthylene. The arylene group can be optionally substituted (a "substituted arylene") with one or more "aryl group substituents" as defined herein, which can be the same or different.

"Aralkylene" refers to a bivalent group that contains both alkyl and aryl groups. For example, aralkylene groups can have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as NR$_3$, NH$_3$, NHR$_2$, and NH$_2$R, wherein R can be alkyl, branched alkyl, cycloalkyl, aryl, alkylene, arylene, aralkylene. Thus, "amino" as used herein can refer to a primary amine, a secondary amine, or a tertiary amine. In some embodiments, one R of an amino group can be a diazeniumdiolate (i.e., NONO).

The terms "cationic amine" and "quaternary amine" refer to an amino group having an additional (i.e., a fourth) group, for example a hydrogen or an alkyl group bonded to the nitrogen. Thus, cationic and quaternary amines carry a positive charge.

The term "alkylamine" refers to the -alkyl-NH$_2$ group.

The term "carbonyl" refers to the —(C=O)— group.

The term "carboxyl" refers to the —COOH group and the term "carboxylate" refers to an anion formed from a carboxyl group, i.e., —COO".

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The term "mercapto" or "thio" refers to the —SH group.

The term "MPTMS" refers to (3-Mercaptopropyl)trimethoxysilane.

The term "AEAP3" refers to N-(2-aminoethyl)-3-aminopropyltrimethoxysilane.

The term "AHAP3" refers to N-(6-aminohexyl)aminopropyltrimethoxysilane.

The term "APTES" refers to 3-aminopropyltriethoxysilane.

The term "BTMS" refers to isobutyltrimethoxysilane.

The term "MAP3" refers to N-methylaminopropyltrimethoxysilane.

The term "TEOS" refers to Tetraethylorthosilicate.

The term "TMOS" refers to Tetramethylorthosilicate

The term "DET3" refers to 3-(trimethoxysilylpropyl)diethylenetriamine.

The term "silyl" refers to groups comprising silicon atoms (Si).

As used herein the term "alkoxysilane" refers to a compound comprising one, two, three, or four alkoxy groups bonded to a silicon atom. For example, tetraalkoxysilane refers to $Si(OR)_4$, wherein R is alkyl. Each alkyl group can be the same or different. An "alkylsilane" refers to an alkoxysilane wherein one or more of the alkoxy groups has been replaced with an alkyl group. Thus, an alkylsilane comprises at least one alkyl-Si bond. The term "fluorinated silane" refers to an alkylsilane wherein one of the alkyl groups is substituted with one or more fluorine atoms. The term "cationic or anionic silane" refers to an alkylsilane wherein one of the alkyl groups is further substituted with an alkyl substituent that has a positive (i.e., cationic) or a negative (i.e. anionic) charge, or can become charged (i.e., is ionizable) in a particular environment (i.e., in vivo).

The term "nitrosothiol," refers to the —SNO group. The prefix "S" in "S-nitrosothiol" indicates that the NO group is attached to the sulfur.

The term "silanol" refers to the Si—OH group.

As used herein, the term "activated silanol" refers to silanol groups that have been exposed to ion bombardment by plasma exposure or by an incident ion beam. Without wishing to be bound by theory, ion bombardment by plasma exposure or by incident ion beam is known to create structural defects on a Si-containing surface. The particles and ions impinging on a Si-containing surface are also known to have a charging effect. It has been proposed that the disordered surface structure is responsible for the increased reactivity of the structure. As disclosed herein, the mesoporous silica nanoparticles were treated with plasma to further expose the surface silanols and enhance the functionalization of the particle with NO donors.

As used herein, the term "etched" refers to the surface morphology of the mesoporous nanoparticles after treatment with plasma. The surface may also be described as rough or containing defects.

As used herein, the term "functionalized particle" or "grafted particle" refers to a particle that bears one or more nitric oxide donors.

The particles of the presently disclosed subject matter can be any shape. Thus, the particles can be spherical, elliptical, or amorphous. The size and shape of the particles is, at least in part, determined by the nature (i.e., the chemical composition) or the method of synthesis of the core.

In embodiments, the NO-releasing particles are nanoparticles. In some embodiments, the term "nanoparticle" is meant to refer to a particle having a diameter of between about 0.5 nm and about 1000 nm. In other embodiments, the term "nanoparticle" is meant to refer to a particle having a diameter of between about 0.25 nm and about 2000 nm or between about 5 nm and about 1500 nm.

The nitric oxide donor can be in the interior or the exterior of the particle. The NO donor can be encapsulated within the pores or on the exterior surface of the mesoporous particle. The NO donor can be associated with a particular region of the particle via non-covalent interactions such as Van der Waals interactions, electrostatic interactions (such as interactions between dipoles or between charged groups), hydrogen bonding, or combinations thereof. Further, the NO donor can be covalently bonded to the particle. In some embodiments, the NO donor is a nitrosothiol, in particular a S-nitrosothiol functional group.

In certain embodiments, the nitric oxide releasing particle has a specific surface area in the range of 10 $m^2$/g to 1500 $m^2$/g. In certain embodiments, the specific surface area is in the range of 10-20 $m^2$/g, 15-20 $m^2$/g, 15-550 $m^2$/g, 15-1050 $m^2$/g, 400-600 $m^2$/g, 500-600 $m^2$/g, 525-575 $m^2$/g, 1000-1050 $m^2$/g, 1000-2000 $m^2$/g, and 1025-1075 $m^2$/g.

In certain embodiments, the nitric oxide releasing particle has a thiol content in the range of 100 µmol/g to 700 µmol/g. In certain embodiments, the thiol content is in the range of 200-550 µmol/g, or 500-550 µmol/g.

In certain embodiments, the nitric oxide releasing particle has a total releasable nitric oxide storage in a range of 0.1-5.0 µmol of nitric oxide per milligram of the nitric oxide releasing particle. In certain embodiments, the nitric oxide releasing particle has a total releasable nitric oxide storage in a range of 0.1-4.0 µmol of nitric oxide per milligram of the nitric oxide releasing particle. In some embodiments, on a µmol of NO per milligram of the nitric oxide donor compound, the nitric oxide releasing particle has a total releasable nitric oxide storage in µmol of NO per milligram of nitric oxide releasing particle of at least 0.1, 0.15, 0.2, 0.5, 0.7, 0.8, 0.9, 1.0, 1.5, 2.0, 3.0, 3.5, 4.0, 5.0, or ranges including and/or spanning the aforementioned values.

In several embodiments, the nitric oxide releasing particle has a half-life for nitric oxide release in the range of 0.1-70 hours. In some embodiments, the half-life is in the range between about 1, 0.25-18 hours, 0.5-13 hours, 1-8 hours, 2-6 hours, or 3-4 hours, 5-15 hours, 15-20 hours, 20-30 hours, 25-30 hours, 25-35 hours, 20-40 hours, or 35-40 hours. In some embodiments, NO-release half-life of the nitric oxide releasing particle is greater than or equal to about: 0.1 hours, 0.25 hours, 0.5 hours, 1 hour, 2 hours, 3 hours, 4 hours, 6 hours, 8 hours, 13 hours, 18 hours, 20 hours, 21 hours, 24 hours, 25 hours, 26 hours, 27 hours, 30 hours, 35 hours, 40 hours, or ranges including and/or spanning the aforementioned values.

In some embodiments, the total duration of NO release is in the range of 0.1-1000 hours. In some embodiments, the total duration is in the range between about 1-30 hours, 35-45 hours, 40-75 hours, 60-80 hours, 85-95 hours, 83-105 hours, 100-500 hours, 250-600 hours, 400-600 hours, 430-800 hours, 500-850 hours, 700-900 hours, 2-27 hours, 20-30 hours, 25-30 hours, 0.25-18 hours, 0.5-13 hours, 1-8 hours, 2-6 hours, or 3-4 hours. In some embodiments, the total duration is at least: 1 hour, 2 hours, 3 hours, 4 hours, 5 hours, 6 hours, 10 hours, 20 hours, 21 hours, 30 hours, 40 hours, 41 hours, 48 hours, 49 hours, 50 hours, 51 hours, 52 hours, 60 hours, 70 hours, 80 hours, 89 hours, 90 hours, 100 hours, 200 hours, 300 hours, 400 hours, 500 hours, 600 hours, 700 hours, 800 hours, or ranges including and/or spanning the aforementioned values. In a certain embodiment, the total duration of NO release is about 20 days. In a certain embodiment, the total duration of NO release is about 30 days.

In some embodiments, the total maximum instantaneous NO flux is in the range of 50 to 25,000 ppb/mg. In some embodiments, the total maximum instantaneous NO flux is in the range between about 50-150 ppb/mg, 100-200 ppb/mg, 100-300 ppb/mg, 250-300 ppb/mg, 100-1050 ppb/mg, 100-23,000 ppb/mg, and 1000-23,000 ppb/mg. In certain embodiments, the maximum NO flux is about 1040 ppb/mg.

In some embodiments, the particle has a polydispersity index of about 0.096. In certain embodiments, the polydispersity index is about 0.090, 0.091, 0.092, 0.093, 0.094, 0.095, 0.097, 0.098, or about 0.099.

In certain embodiments, the particles are encapsulated or coated with a polymer. Such incorporation can be through physically embedding the particles into polymer surfaces, via electrostatic association of particles onto polymeric surfaces, or by covalent attachment of particles onto reactive groups on the surface of a polymer. Alternatively, the particles can be mixed into a solution of liquid polymer precursor, becoming entrapped in the polymer matrix when the polymer is cured. Polymerizable groups can also be used to functionalize the exterior of the particles, whereupon, the particles can be co-polymerized into a polymer during the polymerization process. Suitable polymers into which the NO-releasing particles can be incorporated include polyolefins, such as polystyrene, polypropylene, polyethylene, polytetrafluoroethylene, and polyvinylidene, as well as polyesters, polyethers, polyurethanes, and the like. In particular, polyurethanes can include medically segmented polyurethanes. Such polyurethanes can include hard segments, i.e., moieties that are relatively rigid, and soft segments, i.e., moieties having more degrees of freedom that can exist in a number of alternate, inter-converting conformations. Medically segmented polyurethanes can also include one or more expander moieties, such as alkylene chains, that add additional length or weight to the polymer. Such polyurethanes are also generally non-toxic. One example of a medically segmented polyurethane is TECOFLEX®. In certain embodiments, the particle is coated or encapsulated in polyurethane. In certain embodiments the polyurethane is selected from the group consisting of HP-93 A (very hydrophilic polyurethane), AL25-80A (moderately hydrophilic), and PC35-85A (very hydrophobic). In certain embodiments, the polyurethane is HP-93A.

Polymeric compositions such as polymeric films containing NO-releasing particles can be used to coat a variety of articles, particularly surgical tools, biological sensors, and medical implants to prevent platelet adhesion, to prevent bacterial infection, to act as a vasodilator. These articles can be of use in vascular medical devices, urological medical devised, biliary medical devices, gastrointestinal medical devices, medical devices adapted for placement at surgical sites, and medical devices adapted for placement on skin wounds or openings. Thus, the polymers can be used to coat arterial stents, guide wires, catheters, trocar needles, bone anchors, bone screws, protective platings, hip and joint replacements, electrical leads, biosensors, probes, sutures, surgical drapes, wound dressings, and bandages.

Additionally, polymers containing NO-releasing particles can be used to form the devices, themselves. For example, the polymers can be fashioned into storage bags for blood or tissue or as wound dressings.

In certain embodiments, admixing of the particle or one or more particles with the polymer results in a homogeneous mixture.

In certain embodiments, the subject matter disclosed herein is directed to a composition comprising a collection of particles, wherein said collection comprises one or more nitric oxide releasing particles, and a polymer.

In certain embodiments, the composition comprising one of more nitric oxide releasing particles and a polymer has a total releasable nitric oxide storage in a range of 0.1-5.0 $\mu mol/cm^2$. In certain embodiments, the composition comprising one of more nitric oxide releasing particles and a polymer has a total releasable nitric oxide storage in a range of 0.1-4.0 $\mu mol/cm^2$ or 3-5 $\mu mol/cm^2$. In some embodiments, the composition comprising one of more nitric oxide releasing particles and a polymer has a total releasable nitric oxide storage in $\mu mol/cm^2$ of at least: 0.1, 0.15, 0.2, 0.5, 0.7, 0.8, 0.9, 1.0, 1.5, 2.0, 3.0, 3.5, 4.0, 5.0 $\mu mol/cm^2$, or ranges including and/or spanning the aforementioned values.

In some embodiments, the composition comprising one of more nitric oxide releasing particles and a polymer has a total maximum instantaneous NO flux in the range of 50 to 25,000 ppb/cm$^2$. In some embodiments, the composition comprising one of more nitric oxide releasing particles and a polymer has a total maximum instantaneous NO flux in the range between about 50-150 ppb/cm$^2$, 100-200 ppb/cm$^2$, 100-300 ppb/cm$^2$, 250-300 ppb/cm$^2$, 100-1050 ppb/cm$^2$, 100-23,000 ppb/cm$^2$, and 1000-23,000 ppb/cm$^2$.

In certain embodiments, the composition comprising one of more nitric oxide releasing particles and a polymer retains about 100% of its NO payload upon storage at −20° C. for 96 hours or less. In certain embodiments, the composition comprising one of more nitric oxide releasing particles and a polymer retains about 99%, 98%, 97%, 96%, 95%, 94%, 93%, 92%, 91%, 90%, 85%, 75%, 70%, 65%, 60%, 50%, 40%, 30%, 20%, or 10% of its NO payload upon storage at −20° C. for 96 hours or less.

In certain embodiments, the composition comprising one of more nitric oxide releasing particles and a polymer retains about 90% of its NO payload upon storage at 0° C. for 96 hours or less. In certain embodiments, the composition comprising one of more nitric oxide releasing particles and a polymer retains about 100%, 99%, 98%, 97%, 96%, 95%, 94%, 93%, 92%, 91%, 90%, 85%, 75%, 70%, 65%, 60%, 50%, 40%, 30%, 20%, or 10% of its NO payload upon storage at 0° C. for 96 hours or less.

In certain embodiments, the composition comprising one or more nitric oxide releasing particles and a polymer exhibits less than 1% leaching of the total weight of nitric oxide releasing particles present in the composition. In certain embodiments, the composition exhibits less than 0.01%, 0.1%, 0.2%, 0.3%, 0.4%, 0.5%, 0.6%, 0.7%, 0.8%, 0.9%, 1.1%, 1.2%, 1.3%, 1.4%, 1.5%, 1.6%, 1.7%, 1.8%, 1.9%, or 2.0% leaching of the total weight of nitric oxide releasing particles present in the composition. In certain embodiments, the percentage of particles leached corresponds to a total mass of less than 10 $\mu g/cm^2$ of the total weight of nitric oxide releasing particles present in the composition. In certain embodiments, the percentage of particles leached corresponds to a total mass of less than 5 $\mu g/cm^2$, less than 6 $\mu g/cm^2$, less than 7 $\mu g/cm^2$, less than 8 $\mu g/cm^2$, less than 9 $\mu g/cm^2$, less than 11 $\mu g/cm^2$, or less than 12 $\mu g/cm^2$.

Accordingly, in some embodiments, the presently disclosed subject matter provides a method for the delivery of nitric oxide to a subject, which in some embodiments is intended to treat a disease or condition in a subject in need of treatment thereof. In some embodiments, the presently disclosed subject matter provides a method for the targeted delivery of nitric oxide to a specific site in a subject. Such a site can be specific cells, tissues or organs. Thus, the presently disclosed subject matter provides a method for treating cancer, cardiovascular diseases, and microbial infections; for the inhibition of platelet aggregation and platelet adhesion caused by the exposure of blood to a medical device; for treating pathological conditions resulting from abnormal cell proliferation; transplantation rejections, autoimmune, inflammatory, proliferative, hyperproliferative, vascular diseases; for reducing scar tissue or for inhibiting wound contraction, including the prophylactic and/or therapeutic treatment of restenosis by administering the nitric oxide donor optionally in combination with at least one additional therapeutic agent. The presently disclosed subject matter also provides a method for treating inflammation, pain, fever, gastrointestinal disorders, respiratory disorders, sexual dysfunctions, and sexually transmitted diseases.

In some embodiments, the methods of the presently disclosed subject matter can be useful for treatment of a subject, as defined herein. The subject treated in the presently disclosed subject matter in its many embodiments is a human subject, although it is to be understood that the principles of the presently disclosed subject matter indicate that the presently disclosed subject matter is effective with respect to all vertebrate species, including mammals, which are intended to be included in the term "subject." In this context, a mammal is understood to include any mammalian species in which treatment is desirable, particularly agricultural and domestic mammalian species.

Accordingly, the term "subject" as used herein, refers to any invertebrate or vertebrate species. The methods of the presently disclosed subject matter are particularly useful in the treatment of warm-blooded vertebrates. Thus, the presently disclosed subject matter concerns mammals and birds. More particularly, provided is the treatment and/or diagnosis of mammals, such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, e.g., poultry, such as turkeys, chickens, ducks, geese, guinea fowl, and the like, as they also are of economical importance to humans. Thus, provided is the treatment of livestock, including, but not limited to, domesticated swine (pigs and hogs), ruminants, horses, poultry, and the like.

The presently disclosed therapeutic compositions, in some embodiments, comprise a composition that includes a presently disclosed nitric oxide-releasing nanoparticle and a pharmaceutically acceptable carrier. Suitable compositions include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

In some embodiments, the presently disclosed therapeutic compositions comprise an additional therapeutic agent in combination with the nitric oxide-releasing nanoparticles, wherein the additional therapeutic agent has additional desired therapeutic properties or enhances the therapeutic properties of the nitric oxide-releasing nanoparticles. The additional therapeutic agent can be administered in the same or a different therapeutic composition. Thus, the term "in combination" can refer to the administration of active agents in a single composition or in one or more separate compositions.

The compositions used in the presently disclosed methods can take such forms as suspensions, solutions or emulsions in oily or aqueous vehicles, and can contain formulatory agents, such as suspending, stabilizing and/or dispersing agents. Alternatively, the active ingredient can be in powder form for constitution with a suitable vehicle, e.g., sterile pyrogen-free water, before use.

The therapeutic compositions can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients, such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a therapeutic agent can be formulated in combination with hydrochlorothiazide, and as a pH stabilized core having an enteric or delayed release coating which protects the therapeutic agent until it reaches the target organ.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives, such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations also can contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compounds also can be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). The compounds also can be formulated in rectal compositions (e.g., suppositories or retention enemas containing conventional suppository bases, such as cocoa butter or other glycerides), creams or lotions, or transdermal patches.

Pharmaceutical formulations also are provided which are suitable for administration as an aerosol by inhalation. These formulations comprise a solution or suspension of a NO-releasing particle described herein. The desired formulation can be placed in a small chamber and nebulized. Nebulization can be accomplished by compressed air or by ultrasonic energy to form a plurality of liquid droplets or solid particles comprising the NO-releasing particles. For example, the presently disclosed NO-releasing particles can be administered via inhalation to treat bacterial infections related to cystic fibrosis. Cystic fibrosis-related bacterial infections include, but are not limited to, *Pseudomonas aeruginosa* (*P. aeruginosa*) infections.

Doses

The term "effective amount" is used herein to refer to an amount of the therapeutic composition (e.g., a composition comprising a nitric oxide-releasing particle) sufficient to produce a measurable biological response. Actual dosage levels of active ingredients in an active composition of the presently disclosed subject matter can be varied so as to administer an amount of the active compound(s) that is effective to achieve the desired response for a particular subject and/or application. The selected dosage level will depend upon a variety of factors including the activity of the composition, formulation, the route of administration, combination with other drugs or treatments, severity of the condition being treated, and the physical condition and prior medical history of the subject being treated. Preferably, a minimal dose is administered, and dose is escalated in the absence of dose-limiting toxicity to a minimally effective amount. Determination and adjustment of an effective dose, as well as evaluation of when and how to make such adjustments, are known to those of ordinary skill in the art of medicine.

For administration of a composition as disclosed herein, conventional methods of extrapolating human dosage based on doses administered to a murine animal model can be carried out using the conversion factor for converting the mouse dosage to human dosage: Dose Human per kg=Dose Mouse per kg×12. See Freireich et al., *Cancer Chemother Rep.* 50, 219-244 (1966). Drug doses also can be given in milligrams per square meter of body surface area because this method rather than body weight achieves a good correlation to certain metabolic and excretionary functions. Moreover, body surface area can be used as a common denominator for drug dosage in adults and children as well as in different animal species. See Freireich et al., *Cancer Chemother Rep.* 50, 219-244 (1966). Briefly, to express a mg/kg dose in any given species as the equivalent mg/sq m dose, multiply the dose by the appropriate km factor. In an adult human, 100 mg/kg is equivalent to 100 mg/kg×37 kg/sq m=3700 mg/m².

For additional guidance regarding formulation and dose, see U.S. Pat. Nos. 5,326,902; 5,234,933; PCT International Publication No. WO 93/25521; Berkow et al., *The Merck Manual of Medical Information*, Home ed., Merck Research Laboratories: Whitehouse Station, New Jersey (1997); Goodman et al., *Goodman & Gilman's the Pharmacological Basis of Therapeutics*, 9th ed. McGraw-Hill Health Professions Division: New York (1996); Ebadi, *CRC Desk Reference of Clinical Pharmacology*, CRC Press, Boca Raton, Florida (1998); Katzunq, *Basic & Clinical Pharmacology*, 8th ed. Lange Medical Books/McGraw-Hill Medical Pub. Division: New York (2001); Remington et al., *Remington's Pharmaceutical Sciences*, 15th ed. Mack Pub. Co.: Easton, Pennsylvania (1975); and Speight et al., *Avery's Drug Treatment: A Guide to the Properties, Choice, Therapeutic Use and Economic Value of Drugs in Disease Management*, 4th ed. Adis International: Auckland/Philadelphia (1997); Dutch et al., *Toxicol. Lett.*, 100-101, 255-263 (1998).

Suitable methods for administering to a subject a composition of the presently disclosed subject matter include, but are not limited to, systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

The particular mode of drug administration used in accordance with the methods of the presently disclosed subject matter depends on various factors, including but not limited to the agent and/or carrier employed, the severity of the condition to be treated, and mechanisms for metabolism or removal of the active agent following administration.

The subject matter described herein is directed to the following embodiments:

1. A nitric oxide releasing particle, comprising:
    nitric oxide donors;
    a mesoporous silica network; and
    an exterior surface,
    wherein said nitric oxide donors are present within pores of said mesoporous silica network and on the exterior surface of said particle, and wherein said nitric oxide releasing particle comprises an amount of nitric oxide donors such that the particle exhibits a total nitric oxide release duration of at least 49 hours.
2. The nitric oxide releasing particle of embodiment 1, having a surface area sufficient for said amount of nitric oxide donors such that the particle exhibits a total nitric oxide release duration of at least 49 hours.
3. The nitric oxide releasing particle of embodiment 1 or 2, wherein said silica network comprises a material selected from the group consisting of AEAP3, AHAP3, APTES, BTMS, MAP3, MPTMS, TEOS, TMOS, and DET3.
4. The nitric oxide releasing particle of any one of embodiments 1-3, wherein said silica network comprises TEOS.
5. The nitric oxide releasing particle of any one of embodiments 1-4, wherein said particle morphology is etched by plasma.
6. The nitric oxide releasing particle of any one of embodiments 1-5, wherein said plasma is oxygen plasma.
7. The nitric oxide releasing particle of any one of embodiments 1-6, wherein said particle comprises activated silanols.
8. The nitric oxide releasing particle of any one of embodiments 1-7, wherein said nitric oxide donors are selected from the group consisting of a diazeniumdiolate, a nitrosamine, a hydroxyl nitrosamine, a nitrosothiol, a hydroxyl amine, a hydroxyurea, and combinations thereof.
9. The nitric oxide releasing particle of any one of embodiments 1-8, wherein said nitric oxide donors are a nitrosothiol.
10. The nitric oxide releasing particle of embodiment 9, wherein said nitric oxide donors are an S-nitrosothiol.
11. The nitric oxide releasing particle of any one of embodiments 1-10, wherein said particle exhibits a zeta potential of about −5.4 mV.
12. A collection of particles, wherein said collection comprises two or more particles of any one of embodiments 1-11, wherein said particles are monodisperse having a polydispersity index of about 0.096.

13. The nitric oxide releasing particle of any one of embodiments 1-12, wherein said nitric oxide donors are covalently bound to the pores of said mesoporous silica network and to the exterior surface of said particle.
14. The nitric oxide releasing particle of any one of embodiments 1-13, wherein said nitric oxide donors are associated with the pores of said mesoporous silica network and with the exterior surface of said particle via a non-covalent interaction selected from one of Van der Waals forces, an electrostatic force, hydrogen bonding, and a combination thereof
15. The nitric oxide releasing particle of any one of embodiments 1-14, wherein said nitric oxide releasing particle has a total releasable nitric oxide storage of at least 2.00 µmol of NO per milligram of the nitric oxide releasing particle.
16. The nitric oxide releasing particle of any one of embodiments 1-15, wherein said nitric oxide releasing particle provides a maximum NO flux of about 1040 ppb/mg.
17. The nitric oxide releasing particle of any one of embodiments 1-16, wherein said nitric oxide releasing particle exhibits a half-life of about 26 hours.
18. A method of treating a disease, comprising:
    administering an effective amount of the nitric oxide releasing particle of any one of embodiments 1-17 to a subject in need thereof, wherein said disease is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.
19. A composition comprising a collection of particles, wherein said collection comprises one or more nitric oxide releasing particles of any one of embodiments 1-18, and a polymer.
20. The composition of embodiment 19, wherein said polymer is a polyurethane.
21. The composition of embodiment 19 or 20, wherein said one or more nitric oxide releasing particles is admixed with said polymer.
22. The composition of any one of embodiments 19-21, wherein said composition provides a maximum NO flux in the range of about 100 ppb/cm$^2$ to about 300 ppb/cm$^2$.
23. The composition of any one of embodiments 19-22, wherein said composition exhibits a total nitric oxide release duration of at least 20 days.
24. The composition of any one of embodiments 19-23, wherein said composition has a total releasable nitric oxide storage of at least 2.00 µmol/cm$^2$.
25. The composition of any one of embodiments 19-24, wherein said composition has a total releasable nitric oxide storage of at least 4.00 µmol/cm$^2$.
26. The composition of any one of embodiments 19-25, wherein said composition retains about 100% of its NO payload upon storage at −20° C. for 96 hours or less.
27. The composition of any one of embodiments 19-26, wherein said composition exhibits a nitric oxide release duration that is essentially independent of water uptake.
28. The composition of any one of embodiments 19-27, wherein said composition retains about 90% of its NO payload upon storage at 0° C. for 96 hours or less.
29. The composition of any one of embodiments 19-28, wherein said composition exhibits less than 1% leaching of the total weight of the nitric oxide releasing particles present in said composition.
30. A medical device comprising the composition of any one of embodiments 1-29.
31. The medical device of embodiment 30, wherein the medical device is selected from the group consisting of arterial stents, guide wires, catheters, trocar needles, bone anchors, bone screws, protective platings, hip and joint replacements, electrical leads, biosensors, probes, sutures, surgical drapes, wound dressings and bandages.
32. A pharmaceutical composition comprising the nitric oxide releasing particle of any one of embodiments 1-17 and a pharmaceutically acceptable excipient.

The following examples are offered by way of illustration and not by way of limitation.

EXAMPLES

Materials

All solvents and reagents were analytical-grade and used as received unless noted otherwise. Dimethyl sulfoxide (DMSO), concentrated hydrochloric acid (HCl), cetyltrimethylammonium bromide (CTAB), triethylamine (TEA), sodium nitrite, diethylenetriaminepentaacetic acid (DPTA), and diisopropylethylamine (DIPEA) were purchased from Sigma Aldrich (St. Louis, MO). Anhydrous N,N-dimethylformamide (DMF), anhydrous tetrahydrofuran (THF), ammonium hydroxide (NH$_4$OH, 28 wt %), methanol, (MeOH) and ethanol (EtOH) were purchased from Fisher Scientific (Fair Lawn, NJ). 5,5'-dithiobis-(2-nitrobenzoic acid) (Ellman's reagent) was purchased from Invitrogen Molecular Probes (Eugene, OR). Tetraethylorthosilicate (TEOS) and 3-mercaptopropyltrimethoxysilane (MPTMS) were purchased from Gelest (Morrisville, PA) and stored under nitrogen atmosphere. Polyurethanes HP-93A and PC35-85A were received from Lubrizol (Cleveland, OH). Polyurethane AL25-80A was received from AdvanSource Biomaterials (Wilmington, MA). Nitrogen (N$_2$), argon (Ar), and nitric oxide calibration gas (NO, 25.87 ppm in N$_2$) were purchased from Airgas National Welders (Raleigh, NC). Water was purified using a Millipore Reference water purification system (Bedford, MA) to a resistivity of 18.2 MΩcm and a total organic content of <6 ppb.

Example 1: Synthesis of NO-Releasing Silica Nanoparticles

Synthesis of Nonporous NO-Releasing Silica Nanoparticles

Synthesis of thiol-functionalized nonporous silica nanoparticles was carried out through the Stöber method using MPTMS and TEOS.[26] A MPTMS:TEOS mixture was added dropwise to a solution of ethanol, water and ammonia. The molar ratio of reactants (EtOH:H$_2$O:NH$_4$OH:MPTMS:TEOS) was 333:91.8:561:3:1. The reaction was allowed to proceed for 2 h, followed by washing of the particles with ethanol, and particle collection by centrifuging three times.

Synthesis of Mesoporous Silica Nanoparticles (MSN)

The synthesis of mesoporous silica nanoparticles (MSN) was achieved by combining 175 mL EtOH, 162 mL H$_2$O, 11.8 mL NH$_4$OH, and 280 mg CTAB.[35] This solution was stirred for ~15 min to form the liquid crystal template necessary for the generation of porous particles. The TEOS (1.395 mL) was added as a bolus with additional stirring (2 h) at room temperature. The solution became cloudy white, indicating particle formation. Particles were washed three times with ethanol and collected by centrifugation. Following formation of the TEOS MSNs, CTAB still present in the pores was removed via an ion exchange with ethanolic hydrochloric acid. Particles were dried under vacuum, then treated with oxygen plasma for 2 h to expose surface silanols, facilitating maximum functionalization in subsequent steps. Particles at this point in the synthesis are referred to as pre-grafted MSNs.

Figure 5:
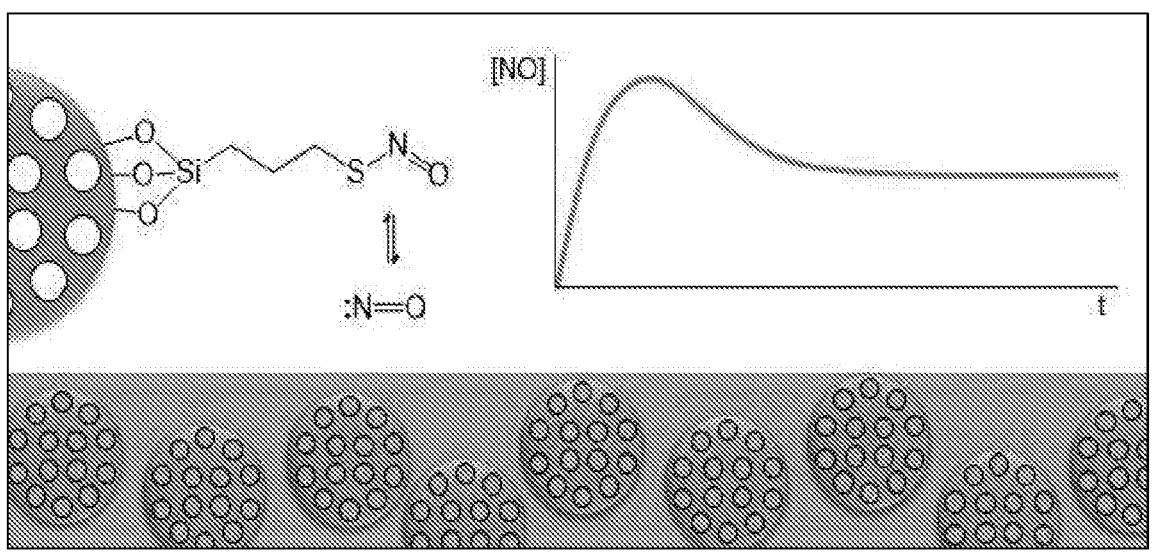
FIG. 5 shows a schematic of a mesoporous silica nitric oxide-releasing nanoparticle functionalized with an S-nitrosothiol NO donor. To the right of the schematic is a plot of NO release as a function of time.

To functionalize the MSNs with thiol groups, a mercaptosilane (MPTMS) was surface grafted onto the bare TEOS MSN scaffold. Approximately 50 mg of MSNs were suspended in 20 mL anhydrous DMF, followed by the addition of 1 μL TEA/mg MSN. The TEA served as a base catalyst. The solution was sonicated to distribute the particles before adding 130 μL MPTMS/mg MSN as a bolus. The flask was immediately set to reflux at 150° C. for 12 h. The solution was then cooled to room temperature, particles were collected by centrifugation with ethanol wash three times, and dried under vacuum. The particles at this stage are referred to as post-grafted MSNs. FIG. 5 shows a schematic of a functionalized MSN.

Nitrosating the Nanoparticles

The next step involved nitrosating the particles via exposure to acidified nitrite. Thiol-modified particles (25 mg) were dissolved in a mixture of 5 mL MeOH and 1 mL HCl (5 M). An aqueous solution (500 μL) of nitrite (50 mg) and DPTA (10 mg) was then added slowly to the particle solution. This mixture was shielded from light and stirred at 0° C. for 1 h. Particles were then collected by centrifugation and washed with −20° C. MeOH three times. The particle batches were dried under vacuum for 45 min to remove all remaining MeOH. Nitrosated particles, deep pink in color, were used immediately after removal from the vacuum box. Care was exercised to minimize ambient light exposure during the nitrosation process, as light may prompt the premature release of NO.

Example 2: Silica Nanoparticle Physiochemical Characterization

Particle morphology and geometric size were determined using a Hitachi S-4700 Cold Cathode Field Emission Scanning Electron Microscope (Pleasanton, CA). Samples in scanning electron micrographs were sputter-coated with 5.0 nm gold/platinum. Specific surface area and pore width of the MSNs were obtained via nitrogen sorption isotherms using a Micrometrics Tristar II 3020 Surface Area and Porosity Analyzer (Norcross, GA). Porosimeter samples were dried at 115° C. for 12 h prior to analysis. The specific surface area was assessed using the Brunauer-Emmett-Teller (BET) method using the adsorption isotherm over the $p/p°$ range of 0.05-0.15. The pore width was measured over the $p/p°$ range of 0.05-0.60 using the Barrett-Joyner-Halenda (BJH) method. Zeta potential of the particles was determined using a Zetasizer Nano ZS Particle Size and Zeta Potential Dynamic Light Scattering Instrument (Malvern, U.K.). Samples were suspended at a concentration of 1 mg mL$^{-1}$ in phosphate buffer at pH 7.4 and sonicated directly prior to analysis. The Ellman's assay was used to determine the free thiol content of modified particles.[26,36] Known masses of particles were added to a solution of DMSO (2.5 mL), MeOH (2 mL), DIPEA (20 μL), and 10 mM Ellman's reagent (1.5 mL, in DMSO). A calibration curve was constructed using known concentrations of L-cysteine. Samples were incubated at room temperature for 1 h, followed by absorbance measurements at 412 nm using a Labsystems MultiskanRC plate reader (Helsinki, Finland).

Example 3: Suspension of Porous and Nonporous Particles in Polyurethane Membranes Polyurethane solutions were prepared by dissolving polyurethane at a concentration of 80 mg mL$^{-1}$ into 3:1 anhydrous THF:DMF, and sonicating at 60° C. Upon full dissolution of the polymer, the solution was cooled to room temperature and particles dispersed into the solution at a range of concentrations (10 mg mL$^{-1}$ to 80 mg mL$^{-1}$), sonicating vigorously to insure homogenous dispersal. Polyurethane membranes were deposited by a loop-casting method in the dark on a stainless steel wire to provide uniform coatings of polyurethane. For each layer, 6.5 μL of the polyurethane solution was pipetted onto a 2 mm steel wire loop. This loop was passed over the wire for a total of seven separate coats, with a drying time of 5 min between each coat. An identical coating technique was used to coat sealed glass capillaries to assess the impact of trace metal ions on NO-release rates. After all coats had been applied, membranes were dried for an additional 1 h, and then stored at −20° C. until use.

Example 4: Nitric Oxide-Release Measurements

Nitric-oxide release was measured via two methods. Instantaneous NO-release was measured in real-time using a Sievers 280i Chemiluminescent Nitric Oxide Analyzer (NOA; CO). The NOA was calibrated before use with a two-point calibration consisting of air passed through an NO zero filter and 25.87 ppm NO in $N_2$ as blank and standard values, respectively. When measuring NO release, either 1 mg of particles or one 7-cm polyurethane-coated wire was added to a sample flask with 30 mL deoxygenated PBS at pH 7.4 and 37° C. The sample flask was shielded from light using aluminum foil to restrict undesirable light-initiated NO release. Nitrogen gas was bubbled through the sample solution at 80 mL min$^{-1}$ to transport liberated NO from the solution to the instrument reaction cell. Measurements were taken until the instrument value fell below a limit of detection of 6 ppb mg$^{-1}$ particles s$^{-1}$ for particles or 0.8 pmol cm membrane$^{-2}$ s$^{-1}$ for particle-doped polyurethanes.

Due to the low, extended NO flux of the RSNO-modified films, an NO-measurement technique with a lower limit of detection was required to better characterize the NO flux profile. The Griess assay was thus used to quantify low-flux NO release as previously described.[37] Briefly, polyurethane-coated wires were incubated in PBS at pH 7.4 at 37° C. in the dark, with aliquots of the soak solution removed at various time-points over the samples' release duration. These samples were assessed by mixing 50 μL sample solution, 50 μL 0.1% w/v aqueous N-(1-napthyl)ethylene diamine, and 50 μL 1% w/v sulfanilamide in 5% v/v aqueous phosphoric acid. This mixture was incubated for 5 min to allow formation of the colored azo dye. Absorbance of the sample solutions was measured at 540 nm on a Labsystem MultiskanRC Microplate Spectrophotometer (Helsinki, Finland). A calibration curve of nitrite from 2-100 μM allowed for indirect quantitative determination of the NO concentration in the polyurethane soak solutions. For the thermal stability study, polyurethane films were stored in microcentrifuge tubes sealed in opaque bags.

Example 5: Film Leaching Analysis

Leaching of the RSNO-modified particles from polyurethane films was characterized using a Teledyne-Leeman Laboratories Prodigy High Dispersion inductively coupled plasma optical emission spectroscopy (ICP-OES; Hudson, NH). Wires coated with particle-doped polyurethane membranes were incubated in PBS at pH 7.4 at 37° C. in the dark. After 21 d, the polyurethane-coated wires were removed and the soak solution was analyzed for silicon content, using the Si emission line at 251.611 nm. Calibration was performed using both sodium silicate standards and MSN standards, with a linear response confirmed from both standard sets over a range of 0.1 to 25 ppm in PBS. The buffer solution used in this experiment was prepared using only polypropylene vessels, as silicic acid from glass containers was previously shown to reach the soak solution and display measurable Si levels.[38]

Example 6: Characterization of MSNs Before and After Grating

The MSNs were characterized before and after MPTMS grafting (Table 1). Zeta potential measurements revealed that the surface of the particles was more neutral after modification, demonstrating the conversion of anionic surface silanols to neutral thiol end-groups. Porosimetry measurements indicated that the surface area of the particle was decreased by almost half after grafting (1041 to 549 m$^2$ cm$^{-1}$), validating intraporous grafting.[35,43] Grafting on both the exterior and interior particle surface was confirmed through a combination of surface charge and surface area characterization methods. Grafting inside of the pores was maximized in order to take advantage of both the large surface area characteristic of the MSNs and the stability provided by the confined intraporous structure.

TABLE 1

Physiochemical characterization of pre- and post-grafted MPTMS:TEOS mesoporous silica nanoparticles.[a]

| MSN Synthesis Stage | Zeta Potential (mV) | Pore Width (Å)[b] | Specific Surface Area (m$^2$ g$^{-1}$)[c] |
|---|---|---|---|
| Pre-Grafting | −32.8 ± 1.7 | 23.29 ± 0.44 | 1041 ± 35 |
| Post-Grafting | −5.4 ± 0.9 | 20.77 ± 1.63 | 549 ± 10 |

[a] Error bars represent standard deviation for n ≥ 3 separate syntheses.
[b] Calculated via BJH analysis of nitrogen adsorption isotherm (p/p° ≤ 0.6).
[c] Determined by BET analysis of nitrogen adsorption isotherms (0.05 ≤ p/p° ≤ 0.15).

Example 7: Morphology Comparison of Porous and Nonporous Particles

Figure 1B:
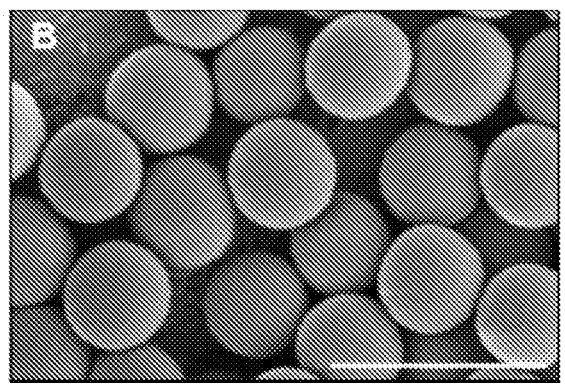
FIG. 1B shows a scanning electron micrograph of MPTMS-functionalized MSNs. The scale bar represents 2 µm.
Figure 1C:
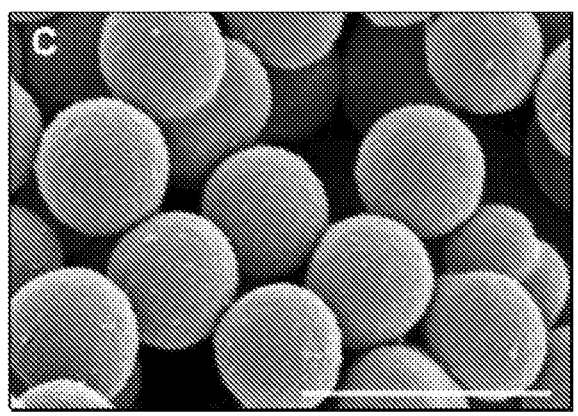
FIG. 1C shows a scanning electron micrograph of non-porous MPTMS:TEOS silica nanoparticles. The scale bar represents 2 µm.

To isolate the effect of the porous structure from that of other morphological characteristics, synthetic parameters were optimized so that the shape and size of both the nonporous and porous particles were identical. Morphological data on the particle size, surface charge, and specific surface area is provided in Table 2. Scanning electron micrographs of the nonporous particles and porous particles pre- and post-grafting allowed visual comparison and confirmation that each particle type had spherical, monodisperse morphologies (FIG. 1a, FIG. 1b, and FIG. 1c). High monodispersity was also indicated by light scattering measurements (~1 μm average size; PDI<0.1). In terms of surface characteristics, the zeta potential was the major difference between the two particles. While the zeta potential of the nonporous system was quite negative (−30.9 mV), the porous particles were more neutral (−5.4 mV). The negative surface charge observed for both particle systems is attributed to anionic surface silanols. The more neutral zeta potential of porous particles indicates greater conversion of negative silanols to neutral thiol end-groups during mercaptosilane functionalization. This difference in the degree of functionalization was confirmed via Ellman's assay, a method that quantifies free thiols. Indeed, the thiol content of the porous particles was more than double that of nonporous particles. From a morphological standpoint, the two particle systems have similar size, shape, and monodispersity but varying surface charge resulting from the degree of surface modification.

TABLE 2

Comparison of nonporous and porous MPTMS:TEOS silica nanoparticle morphology.[a]

| Particle Type | Geometric Size (nm)[b] | PDI[c] | Zeta Potential (mV) | Specific Surface Area (m$^2$ g$^{-1}$)[d] | Thiol content (μmol g$^{-1}$)[e] |
|---|---|---|---|---|---|
| Nonporous | 1172 ± 57 | 0.054 ± 0.011 | −30.9 ± 0.6 | 17.8 ± 1.2 | 231 ± 19 |
| Porous | 1030 ± 52 | 0.096 ± 0.042 | −5.4 ± 0.9 | 549 ± 10 | 537 ± 25 |

[a] Error bars represent standard deviation for n ≥ 3 separate syntheses.
[b] Based on n ≥ 30 particles in SEM images.
[c] Measured using dynamic light scattering.
[d] Determined by BET analysis of nitrogen adsorption isotherms (0.05 ≤ p/p° ≤ 0.15).
[e] Determined by Ellman's assay.

Example 8: NO-Release Comparison of Porous and Nonporous Particles

The NO-release kinetics of the two particle systems were compared to evaluate the impact of pore structure on NO storage and stability. Nitric oxide-release parameters were determined using two complementary methods. While chemiluminescent detection using a Nitric Oxide Analyzer (NOA) allows for real-time NO flux measurements, dynamic initial flux profile, and release kinetics (e.g., half-life) with a relatively low limit of detection (nM), this instantaneous analysis method is not well suited for measuring the lower magnitude NO release typical of stabilized RSNO donors at extended periods. For this reason, the Griess assay, an indirect colorimetric assay that quantifies NO concentrations, was also used to assess NO-release over extended periods. Though the Griess assay has a higher limit of detection (0.5 μM), it is only limited by the ability to differentiate between cumulative NO concentrations at successive time points, which allowed profiling of lower NO fluxes. Together, the full NO-release profiles of the NO-releasing systems were determined, including total payload ([NO]$_T$), maximum flux ([NO]$_{max}$), half-life ($t_{1/2}$), and release duration ($t_d$).[44]

As shown in Table 3, the NO release from the two RSNO-functionalized silica nanoparticles systems was markedly different. Overall, the porous particles had a larger NO payload, longer half-life, and greater release duration than the nonporous analogues. The free thiol content of porous particles correlates directly with the NO payload as more surface thiol groups are available for RSNO conversion. Even after incubation in PBS at 37° C. for ~100 h, the particles still appeared slightly pink to the eye, evidence of intact primary RSNO groups. These results suggest that intraporous RSNO groups may be stabilized to the extent that their decomposition to NO is inhibited even under incubation conditions that should facilitate RSNO breakdown. This was further investigated by exposing the particles to a 10 μM $CuBr_2$ solution; the available $Cu^{2+}$ initiates catalytic decomposition of the RSNOs.[27,45] Copper-based decomposition of RSNOs would neither occur via a radical process nor be influenced by a cage effect. A total purge of NO would be anticipated upon RSNO breakdown. The observed NO payload from the porous particles upon exposure to copper ions increased by >50% to 3.29 μmol $mg^{-1}$, while the observed NO payload of the nonporous particles stayed largely the same. The results of the copper-initiated release indicate that the porous particles do not fully release all of their NO payload under the original incubation conditions. Even though some NO was retained by the MSN scaffold, the NO payload for the porous particles was still nearly twice that of their nonporous counterparts, a clear advantage of porous particles for drug delivery applications.

Thus, the low magnitude, extended NO flux achieved using porous particles holds promise for medical device applications where concerns over lowering inflammation, mitigating infections, and stimulating blood vessel growth are of importance.

Example 9: Comparison of Polyurethane-Based NO Release Using Porous and Nonporous Particles Dispersion of the silica nanoparticles in a polyurethane matrix was characterized to assess the ability to create stable NO-release polymers for medical devices. Polyurethane (PU) is a common biomedical material resulting from its inherent bioinertness and robust mechanical properties.[50,51] Furthermore, polyurethane is available in a range of hydrophobicities to control water uptake. For example, hydrophobic PU coatings have been shown to reduce the rate of biofouling, thrombosis, and bacterial colonization on catheters, stents, and insulin pumps.[52-54] Conversely, hydrophilic polyurethanes are important for certain biosensor designs, where the diffusion of analytes through the polymer matrix is essential for device functionality.[55,56] An NO-releasing system capable of consistent NO release across a range of hydrophobicities would allow for expanded medical device utility. Three polyurethane formulations were used as models of very hydrophilic (HP-93A), moderately hydrophilic (AL25-80A), and very hydrophobic (PC35-85A) PUs. Nitrosated nonporous and porous particles dispersed in these polyurethane solutions were loop cast onto wire substrates. Loop casting results in a reproducible thin, uniform polymeric layer containing particles.[23,57] Nitric oxide release from membranes cast on analogous glass substrates were consistent with those on the steel wire substrates, indicating that any trace metal ions from the wires did not impact NO release (Table 4). Table 5 depicts the NO-release characteristics as a function of polyurethane type.

TABLE 3

NO-release measurements in physiological buffer (PBS, pH 7.4, 37° C.) of MPTMS:TEOS nanoparticles in the absence of light.[a]

| Particle Type | $[NO]_{max}$ (ppb $mg^{-1}$)[b] | $t_{1/2}$ (h)[c] | $t_d$ (h)[d] | $[NO]_T$ (μmol $mg^{-1}$)[e] | $[NO]_{Cu2+}$ (μmol $mg^{-1}$)[f] |
|---|---|---|---|---|---|
| Nonporous | 22800 ± 2400 | 2.92 ± 0.91 | 42.6 ± 3.1 | 1.55 ± 0.17 | 1.71 ± 0.21 |
| Porous | 1040 ± 80 | 26.6 ± 1.6 | 89.1 ± 2.5 | 2.18 ± 0.08 | 3.29 ± 0.14 |

[a]Error bars represent standard deviation for n ≥ 3 separate syntheses.
[b]Maximum instantaneous NO flux.
[c]Half-life of NO release.
[d]NO release duration; time for NO concentrations to reach ≤6 ppb $mg^{-1}$.
[e]Total NO release.
[f]Total NO release in the presence of 10 μM $CuBr_2$.

Another major difference between the two particle systems is their NO-release kinetics. The porous particles were characterized as having a 26-h half-life and total release duration of nearly four days. Generally, the mobility of RSNO groups largely dictates NO-release rates, as a thiyl radical must react with an intact RSNO group to avoid recombination with the NO radical.[46] In this case, the significant difference in NO release (rates) between porous and nonporous particles of the same size and shape suggests that the porous structure also contributes to the prolonged release durations. Primary RSNO groups within the interior pore surface may exist in solvent cages enforced by the surrounding pore structure. When a confined, intraporous RSNO group undergoes photothermal degradation, the likelihood of recombination of the thiyl and NO radicals before NO can diffuse away appears greater than for exterior RSNO groups. The more extended NO-release profile from porous particles also corresponded to a lower maximum NO flux relative to the nonporous particles. Large NO fluxes, as displayed by the nonporous particles and many N-diazeniumdiolate-based silica nanoparticles, generally limit NO-release duration. Additionally, large NO fluxes are associated with pro-inflammatory and cytotoxic processes including apoptotic responses and full cell cycle arrest.[47-49]

TABLE 4

Nitric oxide-release measurements of porous particle-doped polyurethane membranes cast on glass capillaries in physiological buffer (PBS, pH 7.4, 37° C.).[a]

| Substrate | $[NO]_{max}$ (ppb $cm^{-2}$)[b] | $t_{1/2}$ (h)[c] | $[NO]_T$ (μmol $cm^{-2}$)[d] |
|---|---|---|---|
| Glass | 234 ± 33 | 32.5 ± 3.7 | 3.96 ± 0.24 |

[a]80 mg $mL^{-1}$ MPTMS:TEOS MSN.
[b]Maximum instantaneous NO flux.
[c]Half-life of NO release.
[d]Total NO release.

TABLE 5

Nitric oxide-release measurements of polyurethane membranes doped with 80 mg mL$^{-1}$ MPTMS:TEOS MSNs in physiological buffer (PBS, pH 7.4, 37° C.).[a]

| Polyurethane | Water Uptake (mg mg$^{-1}$)[b] | [NO]$_{max}$ (ppb cm$^{-2}$)[c] | t$_{1/2}$ (h)[d] | t$_d$ (d)[e] | [NO]$_T$ (μmol cm$^{-2}$)[f] |
|---|---|---|---|---|---|
| HP-93A | 2.61 ± 0.12 | 254 ± 9 | 37.8 ± 3.1 | 33.2 ± 0.3 | 4.18 ± 0.24 |
| AL25-80A | 0.63 ± 0.14 | 286 ± 14 | 29.1 ± 4.0 | 30.7 ± 0.7 | 2.24 ± 0.63 |
| PC35-85A | 0.18 ± 0.06 | 104 ± 10 | 24.0 ± 2.2 | 29.5 ± 0.4 | 3.94 ± 0.39 |

[a]Error bars represent standard deviation for n ≥ 3 separate syntheses.
[b]Water uptake expressed as mg$_{water}$/mg$_{polyurethane}$
[c]Maximum instantaneous NO flux.
[d]Half-life of NO release.
[e]NO-release duration; time for NO concentrations to reach ≤0.8 pmol cm$^{-2}$.
[f]Total NO release.

Particles doped into polyurethanes were characterized as having prolonged NO-release durations and decreased NO fluxes relative to native particles. These changes are attributed to the polymer matrix serving to confine both exterior and intraporous RSNO groups. Little difference between the NO-release kinetics of the three different particle-doped membranes was observed, even though the three polyurethanes tested essentially span the range of possible hydrophobicities. While the maximum NO flux did not trend with hydrophobicity, the three polyurethanes displayed [NO]$_{max}$ values almost an order of magnitude lower than the native particles (Table 3). The confinement imposed by the polyurethane matrix may suppress rapid degradation of exterior RSNO groups responsible for the initial flux of NO from native particles. The relatively limited NO-release durations from polyurethanes doped with nonporous particles emphasizes the benefit of a pore-associated stabilization to ensure extend release durations in particle-doped polyurethanes (Table 6). The duration of NO release also appeared to be independent of polyurethane water uptake properties as the NO half-life and release duration did not trend with polyurethane hydrophobicity. Therefore, RSNO-based NO release may be especially attractive for medical device coatings. In this manner, a polyurethane composition may be selected based on the particular design criteria of a given device application, not by an NO-release mechanism.

TABLE 6

Nitric oxide-release measurements of polyurethane membranes doped with 80 mg mL$^{-1}$ nonporous MPTMS:TEOS nanoparticles in physiological buffer (PBS, pH 7.4, 37° C.).[a]

| Polyurethane | [NO]$_{max}$ (ppb cm$^{-2}$)[b] | t$_{1/2}$ (h)[c] | t$_d$ (d)[d] | [NO]$_T$ (μmol cm$^{-2}$)[e] |
|---|---|---|---|---|
| HP-93A | 1050 ± 48 | 3.29 ± 0.19 | 7.6 ± 0.4 | 3.04 ± 0.28 |
| AL25-80A | 1244 ± 61 | 3.04 ± 0.39 | 6.1 ± 0.2 | 2.67 ± 0.24 |
| PC35-85A | 892 ± 34 | 2.98 ± 0.88 | 6.9 ± 0.7 | 3.31 ± 0.19 |

[a]Error bars represent standard deviation for n ≥ 3 separate syntheses.
[b]Maximum instantaneous NO flux.
[c]Half-life of NO release.
[d]NO-release duration; time for NO concentrations to reach ≤0.8 pmol cm$^{-2}$.
[e]Total NO release.

Example 10: Temperature Stability of MSN-Doped Polyurethanes

Medical device coatings necessitate robust materials, both prior to and after implantation in the body. The thermal lability of RSNO-particle-doped PU was thus characterized under different storage conditions. Often, the instability of RSNO-based NO-release systems under ambient temperature conditions is pointed to as a shortcoming or disadvantage compared to N-diazeniumdiolate NO donors. Membranes capable of ambient temperature storage would make the use of RSNO-based device coatings more appealing. Thermal stability testing was carried out by exposing light-shielded RSNO-modified MSN-doped HP-93A polyurethane membranes to a range of storage conditions (−20° C., 0° C. and 23° C.) for 96 h.

Figure 2:
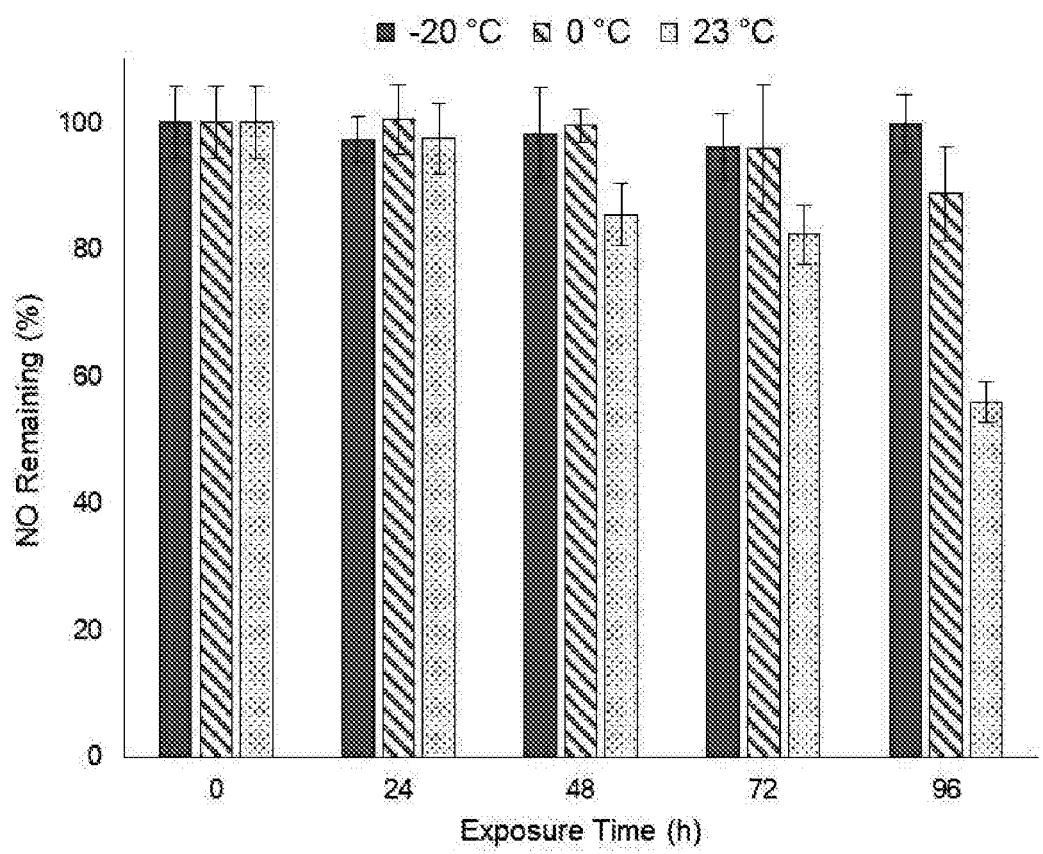
FIG. 2 shows storage stability of RSNO-modified MSN-doped HP-93A polyurethane membranes over 96 h at −20 (solid), 0 (striped), and 23° C. (dotted). n≥6 membranes. All significance is in reference to NO release prior to storage (* $p<0.05$; ** $p<0.01$)
Figure 3:
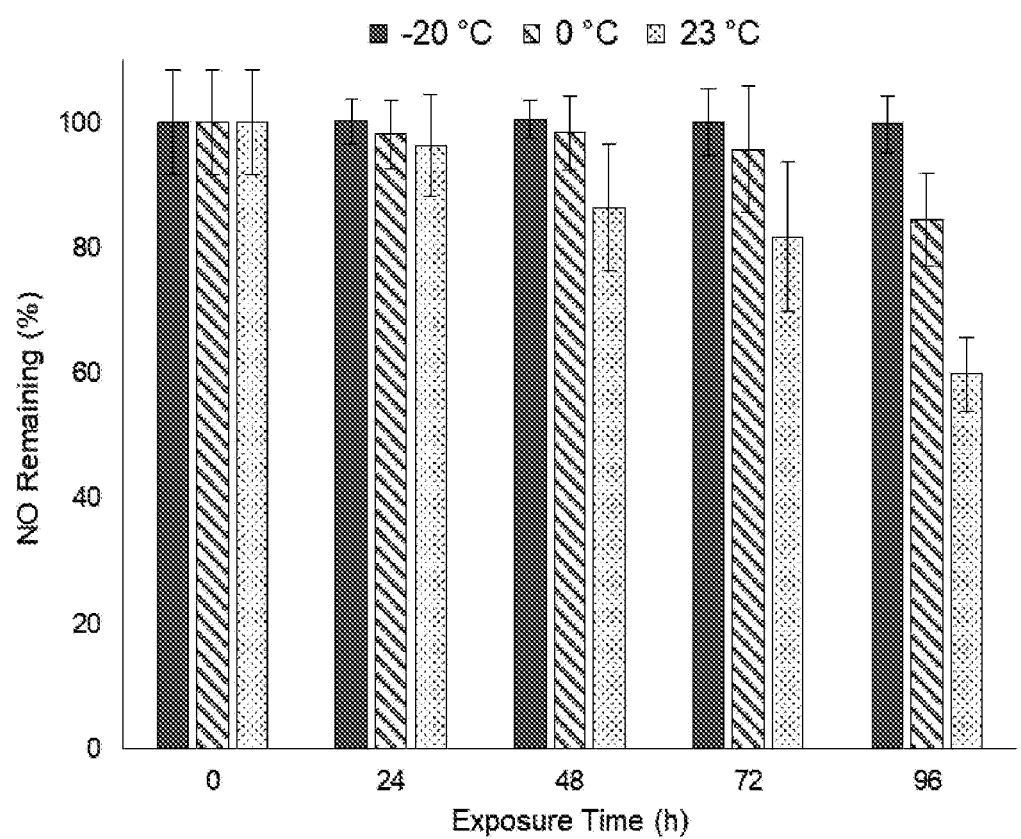
FIG. 3 shows storage stability of RSNO-modified non-porous particle-doped polyurethane membranes for up to 96 h at −20 (solid), 0 (striped), and 23° C. (dotted). n≥6 membranes. All significance is in reference to NO release prior to storage (* $p<0.05$; ** $p<0.01$)

Room temperature storage resulted in reduced NO payloads (FIG. 2), while membranes stored at −20 and 0° C. showed negligible NO payload loss out to 96 h. While storage at room temperature eventually leads to lower NO payloads, storage at 0° C. is sufficient for maintaining NO payloads for at least 4 d. Nonporous particle-doped polyurethanes had similar relative thermal stability versus porous particle-doped polyurethanes (FIG. 3). A solvent cage typically forms in the presence of a solvent, so the cage effect would not significantly contribute to RSNO stabilization during dry storage. Instead, the increased thermal stability of these NO-releasing materials at lower temperatures is more likely due to decreased thermal mobility of the RSNO functional groups. Overall, enhanced thermal stability is desirable for practical NO-release applications, such as those involving medical device coatings.

Example 11: Leaching Investigation of MSN-Doped Polyurethanes

The stability of the RSNO-modified MSN-doped membranes was also assessed with respect to the final fate of the nanoparticles (i.e., leaching). While silica nanoparticles are often used for their bioinertness, silica can still provoke oxidative stress, tissue injury, and endothelial dysfunction.[58-60] A good strategy for avoiding undesirable nanoparticle-associated toxicity is to minimize particle leaching from the membranes.

Figure 4A:
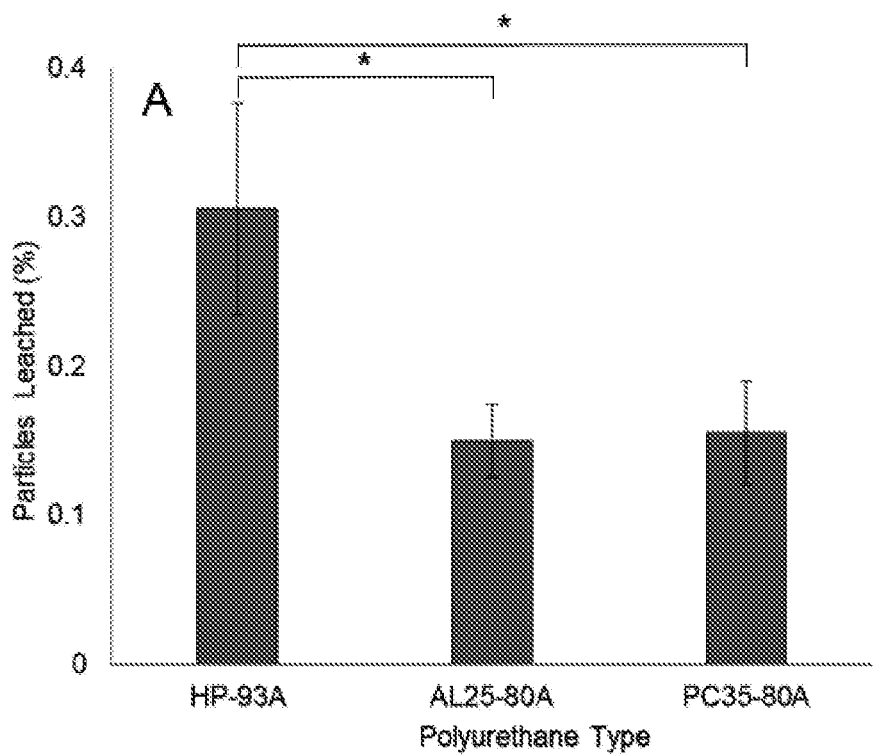
FIG. 4A shows particle leaching as a function of polyurethane membrane composition with 20 mg mL$^{-1}$ MSN; n≥6 membranes after 21-d soaking in solution. (* $p<0.05$)
Figure 4B:
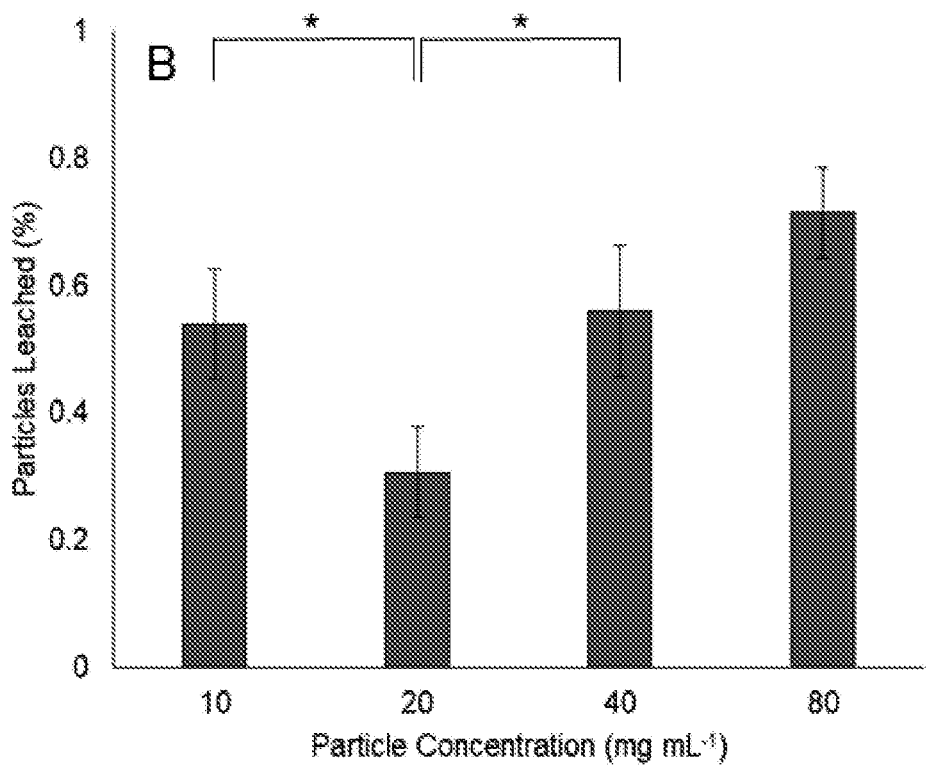
FIG. 4B shows particle leaching as a function of MSN concentrations in HP-93A; n≥6 membranes after 21-d soaking in solution. (* $p<0.05$)

S-nitrosothiol-modified MSN-doped polyurethane membranes were incubated at 37° C. in PBS at pH 7.4 for 21 d. The extent of particle leaching was determined via elemental analysis (ICP-OES) of silicon in the leachate solution (FIG. 4A and FIG. 4B). Comparing across the types of polyurethane, with a constant MSN concentration, the greatest degree of leaching was observed from the most hydrophilic polyurethane, HP-93A. Hydrophilic polyurethanes are known to swell upon water uptake, increasing particle displacement (i.e., leaching).[61] To understand the dependence of particle concentration in the membrane on leaching, HP-93A polymers containing 10 to 80 mg mL$^{-1}$ were soaked in buffer for 21 d. A concentration of 80 mg mL$^{-1}$ particles in the HP-93A was the largest dopant amount tested, as polyurethane did not form a continuous membrane around particles at higher concentrations. While 80 mg $mL^{-1}$ membranes demonstrated the greatest percentage of particles leached, leaching from the membranes was at least partially independent of particle concentration. As shown in FIG. 4A and FIG. 4B, the least leaching was observed for 20 mg $mL^{-1}$ particles, while 10 and 40 mg $mL^{-1}$ particles were statistically equivalent. Increasing hydrophilicity and particle concentration both corresponded with marginally greater leaching magnitudes.

Each of the particle-doped polyurethane compositions tested showed negligible leaching (i.e., <1 wt % leached particles after 21 d incubation). The percentage of particles leached corresponds to a total mass of less than 10 μg $cm^{-2}$.[60] The degree of SNP leaching has often been attributed to both total particle electrical charge and particle surface hydrophobicity, with previous reports suggesting that a high degree of alkanethiol modification counteracts leaching common to silica nanoparticles.[38,61] As the degree of thiol modification of the MSNs described is great, the net particle surface charge is almost neutral (Table 1). Furthermore, the particles are hydrophobic due to the nature of the alkanethiol functional groups decorating their surface. This surface hydrophobicity is distinct from that of more highly charged particles (e.g., amine-based NONOates) known to leach over shorter soak periods.[38] This negligible leaching may allow for expanded use of RSNO-doped polymeric membranes over extended periods, which has not been possible with alternative N-diazeniumdiolate NO donors.

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference.

(1) Witte, M. B.; Barbul, A. Role of Nitric Oxide in Wound Repair. *Am. J. Surg.* 2002, 183, 406-412.

(2) Cooke, J. P. NO and Angiogenesis. *Atherosclerosis* 2003, 4, 53-60.

(3) Wang, Y.; Vaddiraju, S.; Gu, B.; Papadimitrakopoulos, F.; Burgess, D. J. Foreign Body Reaction to Implantable Biosensors. *J. Diabetes Sci. Technol.* 2015, 9, 966-977.

(4) Bogdan, C. Nitric Oxide and the Immune Response. *Nat. Immunol.* 2001, 2, 907-916.

(5) De Groote, M. A.; Fang, F. C. NO Inhibitions: Antimicrobial Properties of Nitric Oxide. Oxford Univ. Press 1995, 21, 162-165.

(6) Hakim, T. S.; Sugimori, K.; Camporesi, E. M.; Anderson, G. Half-Life of Nitric Oxide in Aqueous Solutions with and without Haemoglobin. *Physiol. Meas.* 1996, 17, 267-277.

(7) Varu, V. N.; Tsihlis, N. D.; Kibbe, M. R. Nitric Oxide-Releasing Prosthetic Materials. *Vasc. Endovascular Surg.* 2009, 43, 121-131.

(8) Seabra, A. B.; Durán, N. Nitric Oxide-Releasing Vehicles for Biomedical Applications. *J. Mater. Chem.* 2010, 20, 1624-1637.

(9) Carpenter, A. W.; Schoenfisch, M. H. Nitric Oxide Release: Part II. Therapeutic Applications. *Chem. Soc. Rev.* 2012, 41, 3742-3752.

(10) Zanini, S.; Polissi, A.; Maccagni, E. A.; Dell'Orto, E. C.; Liberatore, C.; Riccardi, C. Development of Antibacterial Quaternary Ammonium Silane Coatings on Polyurethane Catheters. *J. Colloid Interface Sci.* 2015, 451, 78-84.

(11) Wrzeszcz, A.; Dittrich, B.; Haamann, D.; Aliuos, P.; Klee, D.; Nolte, I.; Lenarz, T.; Reuter, G. Dexamethasone Released from Cochlear Implant Coatings Combined with a Protein Repellent Hydrogel Layer Inhibits Fibroblast Proliferation. *J. Biomed. Mater. Res. A* 2014, 102, 442-454.

(12) Norton, L. W.; Koschwanez, H. E.; Wisniewski, N. A.; Klitzman, B.; Reichert, W. M. Vascular Endothelial Growth Factor and Dexamethasone Release from Nonfouling Sensor Coatings Affect the Foreign Body Response. *J. Biomed. Mater. Res. A* 2007, 81, 858-869.

(13) Koh, A.; Carpenter, A. W.; Slomberg, D. L.; Schoenfisch, M. H. Nitric Oxide-Releasing Silica Nanoparticle-Doped Polyurethane Electrospun Fibers. *ACS Appl. Mater. Interfaces* 2013, 5, 7956-7964.

(14) Chou, H. C.; Chiu, S. J.; Liu, Y. L.; Hu, T. M. Direct Formation of S-Nitroso Silica Nanoparticles from a Single Silica Source. *Langmuir* 2014, 30, 812-822.

(15) Lu, Y.; Slomberg, D. L.; Schoenfisch, M. H. Nitric Oxide-Releasing Chitosan Oligosaccharides as Antibacterial Agents. *Biomaterials* 2015, 35, 1716-1724.

(16) Pegalajar-Jurado, A.; Wold, K. A.; Joslin, J. M.; Neufeld, B. H.; Arabea, K. A.; Suazo, L. A.; McDaniel, S. L.; Bowen, R. A.; Reynolds, M. M. Nitric Oxide-Releasing Polysaccharide Derivative Exhibits 8-Log Reduction against *Escherichia coli, Acinetobacter baumannii* and *Staphylococcus aureus*. *J. Control. Release* 2015, 220, 617-623.

(17) Sun, B.; Slomberg, D. L.; Chudasama, S. L.; Lu, Y.; Schoenfisch, M. H. Nitric Oxide-Releasing Dendrimers as Antibacterial Agents. *Biomacromolecules* 2013, 13, 3343-3354.

(18) Rashti, A.; Yahyaei, H.; Firoozi, S.; Ramezani, S.; Rahiminejad, A.; Karimi, R.; Farzaneh, K.; Mohseni, M.; Ghanbari, H. Development of Novel Biocompatible Hybrid Nanocomposites Based on Polyurethane-Silica Prepared by Sol Gel Process. *Mater. Sci. Eng. C* 2016, 69, 1248-1255.

(19) Ibrahim, I. A. M.; Zikry, A. A. F.; Sharaf, M. A. Preparation of Spherical Silica Nanoparticles: Stober Silica. *J. Am. Sci.* 2010, 6, 985-989.

(20) Chen, Y.; Chen, H.; Shi, J. In Vivo Bio-Safety Evaluations and Diagnostic/Therapeutic Applications of Chemically Designed Mesoporous Silica Nanoparticles. *Adv. Mater.* 2013, 25, 3144-3176.

(21) Ren, H.; Colletta, A.; Koley, D.; Wu, J.; Xi, C.; Major, T. C.; Bartlett, R. H.; Meyerhoff, M. E. Thromboresistant/Anti-Biofilm Catheters via Electrochemically Modulated Nitric Oxide Release. *Anal. Chem.* 2015, 25, 368-379.

(22) Koh, A.; Nichols, S. P.; Schoenfisch, M. H. Glucose Sensor Membranes for Mitigating the Foreign Body Response. *J. Diabetes Sci. Technol.* 2011, 5, 1052-1059.

(23) Wolf, A. K.; Qin, Y.; Major, T. C.; Meyerhoff, M. E. Improved Thromboresistance and Analytical Performance of Intravascular Amperometric Glucose Sensors Using Optimized Nitric Oxide Release Coatings. *Chinese Chem. Lett.* 2015, 26, 464-468.

(24) Soto, R. J.; Privett, B. J.; Schoenfisch, M. H. In Vivo Analytical Performance of Nitric Oxide-Releasing Glucose Biosensors. *Anal. Chem.* 2014, 86, 7141-7149.

(25) Slomberg, D. L.; Lu, Y.; Broadnax, A. D.; Hunter, R. A.; Carpenter, A. W.; Schoenfisch, M. H. Role of Size and Shape on Biofilm Eradication for Nitric Oxide-Releasing Silica Nanoparticles. *ACS Appl. Mater. Interfaces* 2013, 5, 9322-9329.

(26) Riccio, D. A.; Nugent, J. L.; Schoenfisch, M. H. Stöber Synthesis of Nitric Oxide-Releasing S-Nitrosothiol-Modified Silica Particles. *Chem. Mater.* 2011, 23, 1727-1735.

(27) Frost, M. C.; Meyerhoff, M. E. Synthesis, Characterization, and Controlled Nitric Oxide Release from S-Nitrosothiol-Derivatized Fumed Silica Polymer Filler Particles. *J. Biomed. Mater. Res.* 2005, 72, 409-419.

(28) De Oliveira, M. G.; Shishido, S. M.; Seabra, A. B.; Morgon, N. H. Thermal Stability of Primary S-Nitrosothiols: Roles of Autocatalysis and Structural Effects on the Rate of Nitric Oxide Release. *J. Phys. Chem. A* 2002, 106, 8963-8970.

(29) Rabinowitch, E.; Wood, W. C. The Collison Mechanism and the Primary Photochemical Process in Solutions. *Trans. Faraday Soc.* 1936, 32, 1381-1387.

(30) Franck, J.; Rabinowitch, E. Free Radicals and the Photochemistry of Solutions. *Trans. Faraday Soc.* 1934, 30, 120-130.

(31) Shishido, S. M.; Seabra, A. B.; Loh, W.; De Oliveira, M. G. Thermal and Photochemical Nitric Oxide Release from S-Nitrosothiols Incorporated in Pluronic F127 Gel: Potential Uses for Local and Controlled Nitric Oxide Release. *Biomaterials* 2003, 24, 3543-3553.

(32) Shishido, S. M.; Oliveira, M. G. Polyethylene Glycol Matrix Reduces the Rates of Photochemical and Thermal Release of Nitric Oxide from S-Nitroso-N-Acetylcysteine. *Photochem. Photobiol.* 2007, 71, 273-280.

(33) Yang, L.; Lu, Y.; Soto, R. J.; Shah, A.; Ahonen, M. J. R.; Schoenfisch, M. H. S-Nitrosothiol-Modified Hyperbranched Polyesters. *Polym. Chem.* 2016, 7, 7161-7169.

(34) Stasko, N. A.; Fisher, T. H.; Schoenfisch, M. H. S-Nitrosothiol-Modified Dendrimers as Nitric Oxide Delivery Vehicles. *Biomacromolecules* 2009, 6, 247-253.

(35) Soto, R. J.; Yang, L.; Schoenfisch, M. H. Functionalized Mesoporous Silica via an Aminosilane Surfactant Ion Exchange Reaction: Controlled Scaffold Design and Nitric Oxide Release. *ACS Appl. Mater. Interfaces* 2016, 8, 2220-2231.

(36) Ellman, G. L. Tissue Sulfhydryl Groups. *Arch. Biochem. Biophys.* 1959, 82, 70-77.

(37) Koh, A.; Riccio, D. A.; Sun, B.; Carpenter, A. W.; Nichols, S. P.; Schoenfisch, M. H. Fabrication of Nitric Oxide-Releasing Polyurethane Glucose Sensor Membranes. *Biosens. Bioelectron.* 2011, 28, 17-24.

(38) Soto, R. J.; Schofield, J. B.; Walter, S. E.; Malone-Povolny, M. J.; Schoenfisch, M. H. Design Considerations for Silica-Particle-Doped Nitric-Oxide-Releasing Polyurethane Glucose Biosensor Membranes. *ACS Sensors* 2017, 2, 140-150.

(39) Liu, T.; Zhang, W.; Yang, X.; Li, C. Hollow Polymer Nanoparticles with S-Nitrosothiols as Scaffolds for Nitric Oxide Release. *J. Colloid Interface Sci.* 2015, 459, 115-122.

(40) Grommersch, B. M.; Pant, J.; Hopkins, S. P.; Goudie, M. J.; Handa, H. Biotemplated Synthesis and Characterization of Mesoporous Nitric Oxide-Releasing Diatomaceous Earth Silica Particles. *ACS Appl. Mater. Interfaces* 2018, 10, 2291-2301.

(41) Denisov, E. T. Cage Effects in a Polymer Matrix. *Macromol. Chem. Phys.* 1984, 8, 63-78.

(42) Minko, S. Grafting on Solid Surfaces: "Grafting to" and "Grafting from" Methods. In *Polymer Surfaces and Interfaces;* 2008; pp 215-234.

(43) Kruk, M.; Jaroniec, M. Gas Adsorption Characterization of Ordered Organic-Inorganic Nanocomposite Materials. *Chem. Mater.* 2001, 13, 3169-3183.

(44) Coneski, P. N.; Schoenfisch, M. H. Nitric Oxide Release: Part III. Measurement and Reporting. *Chem. Soc. Rev.* 2012, 41, 3753-3758.

(45) Stamler, J. S.; Toone, E. J. The Decomposition of Thionitrites. *Curr. Opin. Chem. Biol.* 2002, 6, 779-785.

(46) Williams, D. L. H. The Chemistry of S-Nitrosothiols. *Acc. Chem. Res.* 1999, 32, 869-876.

(47) Thomas, D. D.; Ridnour, L. A.; Isenberg, J. S.; Flores-Santana, W.; Switzer, C. H.; Donzelli, S.; Hussain, P.; Vecoli, C.; Paolocci, N.; Ambs, S.; Colton, C. A.; Harris, C. C.; Roberts, D. D.; Wink, D. A. The Chemical Biology of Nitric Oxide: Implications in Cellular Signaling. *Free Radic. Biol. Med.* 2008, 45, 18-31.

(48) Cleeter, M. W.; Cooper, J. M.; Darley-Usmar, V. M.; Moncada, S.; Schapira, A. H. V. Reversible Inhibition of Cytochrome c Oxidase, the Terminal Enzyme of the Mitochondrial Respiratory Chain, by Nitric Oxide. Implications for Neurodegenerative Diseases. *Fed. Eur. Biochem. Soc. Lett.* 1994, 345, 50-54.

(49) Frungillo, L.; De Oliveira, J. F. P.; Saviani, E. E.; Oliveira, H. C.; Martinez, M. C.; Salgado, I. Modulation of Mitochondrial Activity by S-Nitrosoglutathione Reductase in *Arabidopsis thaliana* Transgenic Cell Lines. *Biochim. Biophys. Acta* 2013, 1827, 239-247.

(50) Akindoyo, J. O.; Beg, M. D. H.; Ghazali, S.; Islam, M. R.; Jeyaratnam, N.; Yuvaraj, A. R. Polyurethane Types, Synthesis and Applications—a Review. *RSC Adv.* 2016, 6, 114453-114482.

(51) Davis, F. J.; Mitchell, G. R. Polyurethane Based Materials with Applications in Medical Devices. In *Bio-Materials and Prototyping Applications in Medicine;* 2008; pp 27-48.

(52) Seo, E.; Na, K. Polyurethane Membrane with Porous Surface for Controlled Drug Release in Drug Eluting Stent. *Biomater. Res.* 2014, 18, 15.

(53) Treter, J.; Macedo, A. J. Catheters: A Suitable Surface for Biofilm Formation. In *Science Against Microbial Pathogens: Communicating Current Research and Technological Advances;* 2011; pp 835-842.

(54) Haj-Ahmad, R.; Khan, H.; Arshad, M. S.; Rasekh, M.; Hussain, A.; Walsh, S.; Li, X.; Chang, M. W.; Ahmad, Z. Microneedle Coating Techniques for Transdermal Drug Delivery. *Pharmaceutics* 2015, 7, 486-502.

(55) Vadgama, P.; Peteu, S. *Detection Challenges in Clinical Diagnostics*; RSC Publishing, 2013.

(56) Fischer, U. Fundamentals of Glucose Sensors. *Diabet. Med.* 1991, 8, 309-321.

(57) Ward, W. K.; Jansen, L. B.; Anderson, E.; Reach, G.; Klein, J. C.; Wilson, G. S. A New Amperometric Glucose Microsensor: In Vitro and Short-Term in Vivo Evaluation. *Biosens. Bioelectron.* 2002, 17, 181-189.

(58) Murugadoss, S.; Lison, D.; Godderis, L.; Van Den Brule, S.; Mast, J.; Brassinne, F.; Sebaihi, N.; Hoet, P. H. Toxicology of Silica Nanoparticles: An Update. *Arch. Toxicol.* 2017, 91, 2967-3010.

(59) Yu, T.; Greish, K.; McGill, L. D.; Ray, A.; Ghandehari, H. Influence of Geometry, Porosity, and Surface Characteristics of Silica Nanoparticles on Acute Toxicity: Their Vasculature Effect and Tolerance Threshold. *ACS Nano* 2012, 6, 2289-2301.

(60) Lin, Y. S.; Haynes, C. L. Impacts of Mesoporous Silica Nanoparticle Size, Pore Ordering, and Pore Integrity on Hemolytic Activity. *J. Am. Chem. Soc.* 2010, 132, 4834-4842.

(61) Dolatzadeh, F.; Jalili, M. M.; Moradian, S. Influence of Various Loadings of Hydrophilic or Hydrophobic Silica Nanoparticles on Water Uptake and Porosity of a Polyurethane Coating. *Mater. Corros.* 2013, 64, 609-618.

Efforts have been made to ensure accuracy with respect to numbers used (e.g., amounts, temperature, etc.) but some experimental errors and deviations should be accounted for.

One skilled in the art will recognize many methods and materials similar or equivalent to those described herein, which could be used in the practicing the subject matter described herein. The present disclosure is in no way limited to just the methods and materials described.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller rangers is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A nitric oxide releasing particle, comprising:
   nitric oxide donors;
   a mesoporous silica network; and
   an exterior surface,
   wherein said nitric oxide donors are present within pores of said mesoporous silica network and on the exterior surface of said particle,
   wherein said nitric oxide releasing particle comprises an amount of nitric oxide donors such that the particle exhibits a total nitric oxide release duration of at least 49 hours, and
   wherein said nitric oxide donors are nitrosothiols.

2. The nitric oxide releasing particle of claim 1, having a surface area sufficient for said amount of nitric oxide donors such that the particle exhibits a total nitric oxide release duration of at least 49 hours.

3. The nitric oxide releasing particle of claim 1, wherein said silica network comprises a material selected from the group consisting of N-(2-aminoethyl)-3-aminopropyltrimethoxysilane (AEAP3), N-(6-aminohexyl)aminopropyltrimethoxysilane (AHAP3), 3-aminopropyltriethoxysilane (APTES), isobutyltrimethoxysilane (BTMS), N-methylaminopropyltrimethoxysilane (MAP3), (3-mercaptopropyl)trimethoxysilane (MPTMS), tetraethylorthosilicate (TEOS), tetramethylorthosilicate (TMOS), and 3-(trimethoxysilylpropyl)diethylenetriamine (DET3).

4. The nitric oxide releasing particle of claim 1, wherein said silica network comprises TEOS.

5. The nitric oxide releasing particle of claim 1, wherein said particle is etched by plasma.

6. The nitric oxide releasing particle of claim 5, wherein said plasma is oxygen plasma.

7. The nitric oxide releasing particle of claim 1, wherein said particle comprises activated silanols.

8. The nitric oxide releasing particle of claim 1, wherein said particle exhibits a zeta potential of about −5.4 mV.

9. A collection of particles, wherein said collection comprises two or more particles of claim 1, wherein said particles are monodisperse having a polydispersity index of about 0.096.

10. The nitric oxide releasing particle of claim 1, wherein said nitric oxide donors are covalently bound to the pores of said mesoporous silica network and to the exterior surface of said particle.

11. The nitric oxide releasing particle of claim 1, wherein said nitric oxide donors are associated with the pores of said mesoporous silica network and with the exterior surface of said particle via a non-covalent interaction selected from one of Van der Waals forces, an electrostatic force, hydrogen bonding, and a combination thereof.

12. The nitric oxide releasing particle of claim 1, wherein said nitric oxide releasing particle has a total releasable nitric oxide storage of at least 2.00 μmol of NO per milligram of the nitric oxide releasing particle.

13. The nitric oxide releasing particle of claim 1, wherein said nitric oxide releasing particle provides a maximum NO flux of about 1040 ppb/mg.

14. The nitric oxide releasing particle of claim 1, wherein said nitric oxide releasing particle exhibits a half-life of about 26 hours.

15. A method of treating a disease, comprising:
    administering an effective amount of the nitric oxide releasing particle of claim 1 to a subject in need thereof, wherein said disease is selected from the group consisting of a cancer, a cardiovascular disease, a microbial infection; platelet aggregation and platelet adhesion caused by the exposure of blood to a medical device; pathological conditions resulting from abnormal cell proliferation; transplantation rejections, autoimmune diseases, inflammation, vascular diseases; scar tissue; wound contraction, restenosis, pain, fever, gastrointestinal disorders, respiratory disorders, sexual dysfunctions, and sexually transmitted diseases.

16. A composition comprising a collection of particles, wherein said collection comprises one or more nitric oxide releasing particles of claim 1, and a polymer.

17. A medical device comprising the composition of claim 16.

18. A pharmaceutical composition comprising the nitric oxide releasing particle of claim 1 and a pharmaceutically acceptable excipient.

* * * * *